United States Patent [19]

Vogt

[11] 4,076,818
[45] Feb. 28, 1978

[54] PYRAZOLO [1,5-C]QUINAZOLINE DERIVATIVES AND RELATED COMPOUNDS

[75] Inventor: B. Richard Vogt, Yardley, Pa.

[73] Assignee: E. R. Squibb & Sons, Inc., Princeton, N.J.

[21] Appl. No.: 702,364

[22] Filed: Jul. 2, 1976

[51] Int. Cl.² .................. A61K 31/305; C07D 487/04
[52] U.S. Cl. ............................. 424/251; 260/256.4 F
[58] Field of Search ................. 260/256.4 F; 424/251

[56] References Cited

U.S. PATENT DOCUMENTS

| | | | |
|---|---|---|---|
| 3,171,740 | 3/1965 | Menzel et al. | 260/256.4 F |
| 3,810,894 | 5/1974 | Kranz et al. | 260/256.4 F |
| 3,890,324 | 6/1975 | Katner | 260/256.4 Q |
| 3,895,027 | 7/1975 | Katner | 260/251 QB |
| 3,897,434 | 7/1975 | Katner | 260/256.4 Q |
| 3,899,508 | 8/1975 | Wikel | 260/310 R |
| 3,903,106 | 9/1975 | Katner | 260/251 QB |
| 4,002,755 | 1/1977 | Yamamoto et al. | 260/256.4 F |

Primary Examiner—Donald G. Daus
Assistant Examiner—James H. Turnipseed
Attorney, Agent, or Firm—Lawrence S. Levinson; Merle J. Smith; Burton Rodney

[57] ABSTRACT

Compounds are provided having the structure

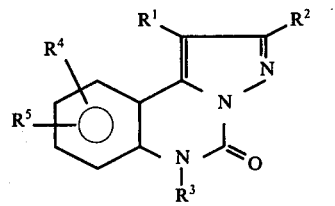

I wherein $R^1$ and $R^2$ may be the same or different and $R^1$ is hydrogen, alkyl of 1-3 carbons, phenyl optionally substituted by $R^4$ or

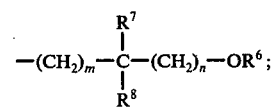

$R^2$ is

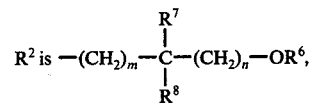

hydrogen, lower alkyl or phenyl optionally substituted by $R^4$ with the proviso that at least one of $R^1$ and $R^2$ is

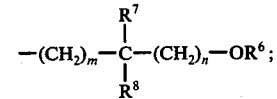

$R^3$ is hydrogen, lower alkyl, benzyl or phenyl optionally substituted by $R^4$; and $R^4$ and $R^5$ are the same or different and represent hydrogen, lower alkyl, lower alkoxy, alkanoyloxy, benzyloxy, hydroxy, halogen (Cl, Br and F), nitro, and trifluoromethyl; $R^6$ is hydrogen, lower alkyl, alkanoyl, aroyl, aralkanoyl, aralkyl or phenyl; and $R^7$, $R^8$, $m$ and $n$ are as defined hereinafter. These compounds are useful as anti-allergics.

11 Claims, No Drawings

PYRAZOLO [1,5-C]QUINAZOLINE DERIVATIVES AND RELATED COMPOUNDS

The present invention relates to pyrazolo[1,5-c]quinazoline derivatives of the structure

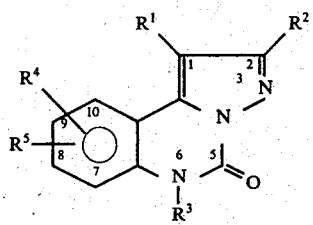

wherein $R^1$ and $R^2$ may be the same or different, and $R^1$ represents hydrogen, lower alkyl, phenyl optionally substituted with $R^4$, or

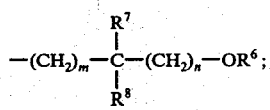

and

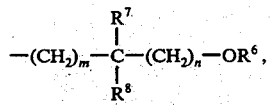

hydrogen, lower alkyl, phenyl optionally substituted with $R^4$, with the proviso that at least one of $R^1$ and $R^2$ is

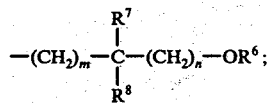

$R^3$ is hydrogen, lower alkyl, benzyl or phenyl optionally substituted by an $R^4$ radical as defined below;

$R^4$ and $R^5$ may be the same or different and are hydrogen, lower alkyl (1–4 carbons), lower alkoxy (1–4 carbons), hydroxy, alkanoyloxy (1–4 carbons),

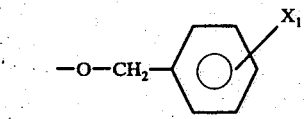

($X_1$ is hydrogen, lower alkoxy (1–4 carbons), Cl, F, Br, $CF_3$ or $NO_2$;

$R^6$ is hydrogen, lower alkyl (1–4 carbons)), alkanoyl, aryl-alkanoyl, aryl-lower alkyl, phenyl optionally substituted by $X_1$, or aroyl;

$R^7$ and $R^8$ may be the same or different and represent hydrogen, lower alkyl containing 1–3 carbons, phenyl optionally substituted with $X_1$ or benzyl optionally substituted with $X_1$, or $R^7$ and $R^8$ taken together can be a single cycloalkyl ring of 3–7 carbons, e.g., cyclopropyl, cyclobutyl, cyclopentyl, cyclohexyl, or cycloheptyl;

$(CH_2)_m$ and $(CH_2)_n$ represent a single bond or straight or branched chain alkylene radicals; and $m$ and $n$ represent the number of carbons in the longest normal chain and may be the same or different and are 0 to 10, preferably 0 to 5, but m plus n is 10 or less, preferably 0 to 5.

With respect to the radical

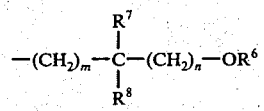

(hereinafter referred to as $Z$-$OR^6$), $R^6$ may be hydrogen and thus primary, secondary and tertiary alcohols may be represented thereby. In addition, $R_6$ may be alkanoyl

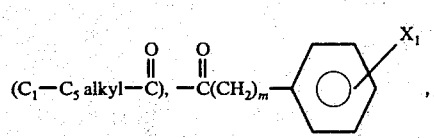

lower alkyl (1–4 carbons), aryl-lower alkyl, or

wherein $X_1$ is as defined above.

Preferred are those compounds wherein $R^2$ is $Z$-$OR^6$

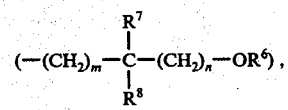

wherein $R^6$ is hydrogen or lower alkanoyl, and $R^1$ is hydrogen or Z-$OR^6$ wherein $R^6$ is hydrogen or lower alkanoyl (in which case $R^2$ may be phenyl), $R^3$ is hydrogen or lower alkyl, $R^4$ and $R^5$ are hydrogen, or one of $R^4$ and $R^5$ is halogen such as Cl, or lower alkoxy such as methoxy.

Most preferred are those compounds of formula I wherein $R^1$ is hydrogen or —$CH_2OH$, and $R^2$ is

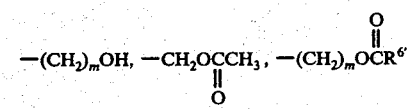

or phenyl, and $R^3$ is hydrogen or lower alkyl, and $R^4$ and $R^5$ are hydrogen and/or methoxy.

Thus, compounds included among those most preferred have the following formulae:

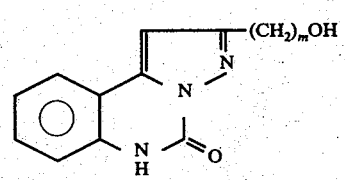

and

-continued

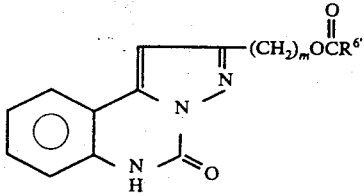

(wherein $R^{6'}$ is hydrogen, methyl, ethyl, propyl or butyl)

Unless otherwise indicated the term "lower alkyl" or "alkyl" as employed herein includes both straight and branched chain radicals of up to eight carbon atoms, for instance, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, and the like.

Unless otherwise indicated, the term "ldower alkoxy" or "alkoxy" includes straight and branched chain radicals which correspond to the above lower alkyl groups attached to an oxygen atom.

Unless otherwise indicated, the term "lower alkanoyl" or "alkanoyl" as employed herein includes any of the above lower alkyl groups linked to a carbonyl group.

Unless otherwise indicated, the term "aryl" as employed herein contemplates monocyclic carbocyclic aryl radicals, for instance, phenyl and substituted phenyl radicals, such as lower alkyl phenyl (e.g., o-, m- or p-tolyl, ethylphenyl, butylphenyl, and the like), di(-lower alkyl)phenyl (e.g., 2,4-dimethylphenyl, 3,5-diethylphenyl, and the like), halophenyl (e.g., chlorophenyl, bromophenyl, iodophenyl, fluorophenyl).

Unless otherwise indicated, the term "aroyl" includes any of the above aryl groups linked to a carbonyl group.

The compounds of Formula I of the invention may be prepared by several methods.

One such method involves the preparation of compounds of the structure

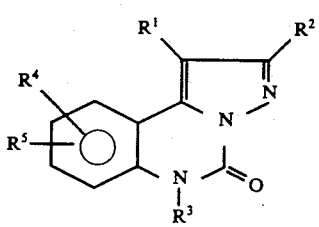

wherein $R^1$ to $R^5$ are as defined hereinbefore. This method (hereinafter caled the "first method") involves reacting a substituted acetylene of formula III with a 3-diazoindol-2(3H)one of formula II in accordance with the following reaction scheme:

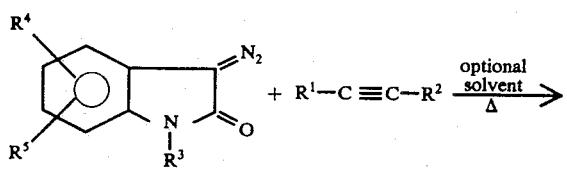

II    III

-continued

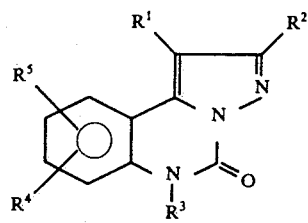

I

The reaction can be carried out in an excess of the acetylenic compound or in an optional solvent which is essentially inert to both of the reactants. Examples of suitable optional solvents include, among others, aliphatic hydrocarbons, such as pentane, hexane, octane, and the like; aromatic hydrocarbons, such as benzene, toluene, the xylenes, and the like; halogenated hydrocarbons, such as methylene chloride, chloroform, carbon tetrachloride, ethylene dichloride, chlorobenzene, bromobenzene, and the like; ethers, such as diethyl ether, diisopropyl ether, methyl butyl ether, tetrahydrofuran, 1,4-dioxane and the like; aliphatic esters, such as methyl acetate, ethyl acetate, butyl acetate, and the like; and miscellaneous solvents, such as N,N-dimethylacetamide, dimethyl sulfoxide, and the like. The aromatic hydrocarbons, such as benzene and toluene and the chlorinated hydrocarbons, such as methylene chloride are preferred. The amount of solvent employed is not critical, but should be sufficient to permit adequate agitation. Typically, the weight-to-volume ratio of reactants to solvent is at least about 1:2 and preferably at least about 1:3, although larger volumes of solvent can be employed if desired. The molar ratio of substituted acetylene to 3-diazoindol-2(3H)-one can vary from about 1:1 to about 1:100. Preferably, the molar ratio will be in the range of from about 1:1 to about 1:40. Reaction time, while to some extent temperature-dependent, can vary from about 15 minutes to about 48 hours. Preferably, the reaction time will be in the range of from about 15 minutes to about 30 hours. Th reaction is normally carried out at an elevated temperature, i.e., from about 40° C to about 150° C, conveniently at the reflux temperature of the solvent, if used, or below about 150° C. A reaction temperature of from about 70° C to about 120° C is preferred. Isolation of the compounds of formula I is accomplished by standard procedures. With the preferred optional solvents, the pyrazolo[1,5-c]quinazolin-5-(6H)-one is relatively insoluble at ambient temperature or lower, and isolation of the reaction product is accomplished by cooling the reaction mixture and removing the precipitate.

In the absence of solvent, the remaining excess substituted acetylene can be optionally removed by distillation in vacuo; the product is isolated by triturating the distillation residue wih a preferred solvent followed by filtration of the precipitated product. If desired, the pyrazolo[1,5-c]quinazolin-5-(6H)-one can be recrystallized from additional reaction solvent.

Another synthesis of compounds of formula I starts with the preparation of compounds of formula V wherein

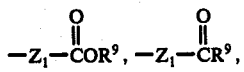

H, alkyl (1–2 carbons), and

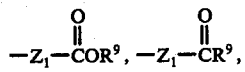

H, alkyl (2–4 carbons) or phenyl, and $Z_1$ is a single bond or Z as defined hereinbefore, and $R^9$ is hydrogen, phenyl, halogen, lower alkyl or

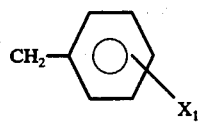

Where the $R_1^1$ or $R_1^2$ groups represent

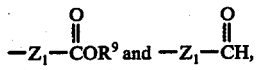

then the total number of carbons in the $Z_1$ group will be 3 or less. Where $R_1^1$ or $R_1^2$ is

wherein $R^9$ is lower alkyl or

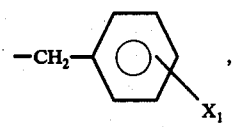

then the total number of carbon atoms in the

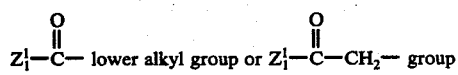

will be 4 or less. Compounds of formula V are prepared by reacting a substituted acetylene (IV) with a 3-diazoindol-2(3H)-one (II) (in a fashion similar to that of the first method) in accordance with the following reaction scheme

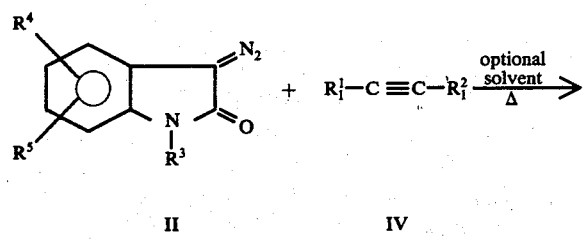

II    IV

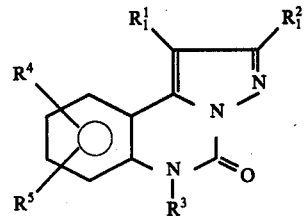

V wherein $R_1^1$ and $R_1^2$ are as defined above. In the examples where $Z_1$ is a single bond, the reaction is preferably carried out in a solvent and the mole ratio of substituted acetylene to 3-diazoindol-2(3H)-one is preferably in the range of 1:1 to about 3:1.

The preferred method of obtaining compounds of formula IV wherein $R^2$ contains a carboxylic acid group involves reacting a substituted acetylene in which $R_1^2$ is lower alkoxycarbonyl with the desired 3-diazoindol-2(3H)-one and selectively hydrolyzing the pyrazolo[1,5-c]quinazolin-5(6H)-one-2-carboxylate ester thus obtained to the free acid. Appropriate conditions are employed which minimize ring opening to the pyrazole-3-carboxylic acid as described hereinbelow.

The substituted acetylene preferably reacts with the 3-diazoindol-2(3H)-one to give a pyrazolo[1,5-c]quinazolin-5-(6H)-one having $R_1^1$ in the 1-position. However, reverse addition can occur which results in $R_1^2$ being in the 1-position. Such reverse addition is not favored, and when $R_1^1$ is hydrogen or lower alkoxycarbonyl, little if any reverse addition product is formed. The resence of reverse addition compound is not detrimental to the isolation and purification of the desired product. However when $R_1^1$ is $C_1$-$C_4$ alkyl, phenyl, or monosubstituted phenyl, the amount of reverse addition product which is formed increase with increasing bulk of $R_1^1$.

The substituted acetylenes employed in the abovedescribed processes in general are commercially available or readily prepared by well-known procedures. Examples of suitable substituted acetylenes include, among others, 3-iso-butyl-5-methyl-3-hydroxy-1-hexyne, 2-butyn-1-ol, 3-butyn-1-ol, 3-butyn-2-ol, 2-decyn-1-ol, 3-decyn-1-ol, diisopropyl ethynyl carbinol, 3,6-dimethyl-1-heptyn-3-ol, 2,5-dimethyl-3-hexyn-2-ol, 3,5-dimethyl-1-hexyn-3-ol, 3,4-dimethyl-1-pentyn-3-ol, 3-ethyl-1-heptyn-3-ol, 4-ethyl-1-hexyn-3-ol, 3-ethyl-5-methyl-1heptyn-3-ol, 4-ethyl-1-octyn-3-ol, 3-ethyl-1-pentyn-3ol (diethyl ethynyl carbinol), 1-heptyn-3-ol, 2-heptyn-1-ol, 2-heptyn-4-ol, 3-heptyn-1-ol, 4-heptyn-2-ol, 4-heptyn-3-ol, 5-heptyn-3-ol, 1-hexyn-3-ol, 2-hexyn-1-ol, 3-hexyn-1-ol, 3-hexyn-2-ol, 4-hexyn-2-ol, 4-hexyn-3-ol, 5-hexyn-1-ol, 5-hexyn-3-ol, methyl-n-amyl ethynyl carbinol, 2-methyl-3-butyn-2-ol, 3-methyl-1-heptyn-3-ol, 3-methyl-4-heptyn-3-ol, 3-methyl-1-butyn-3-ol, 3,5-dimethyl-1-hexyn-3-ol, 3,6-dimethyl-1-heptyn-3-ol,
4-methyl-1-heptyn-3-ol, 4-methyl-2-heptyn-4-ol,
2-methyl-3-hexyn-2-ol, 3-methyl-1-hexyn-3-ol,
3-methyl-4-hexyn-3-ol, 5-methyl-1-hexyn-3-ol,
5-methyl-3-hexyn-1-ol,
3-methyl-1-nonyn-3-ol, 2-methyl-3-octyn-2-ol,
3-methyl-1-octyn-3-ol, 4-methyl-2-octyn-4-ol,
4-ethyl-1-octyn-3-ol, 2-methyl-3-pentyn-2-ol,
3-methyl-1-pentyn-3-ol, 4-methyl-1-pentyn-3-ol,
2-nonyn-1-ol, 3-nonyn-1-ol, 5-nonyn-3-ol, 1-octyn-3-ol,
2-octyn-1-ol, 3-octyn-1-ol, 4-octyn-2-ol, 5-octyn-3-ol,
1-pentyn-3-ol, 2-pentyn-1-ol, 3-pentyn-1-ol,
3-pentyn-2-ol, 4-pentyn-1-ol, 4-pentyn-2-ol,
propargyl alcohol (2-propyn-1-ol), 3-iso-propyl-3-hydroxy-4-methyl-1-pentyne, 3,4,4-trimethyl-1-pentyn-3-ol,
3-methyl-1-nonyn-3-ol, 1,3-diphenyl-1-butyn-3-ol,
diphenyl ethynyl carbinol,
methyl phenyl ethynyl carbinol, 1-phenyl-3-butyn-1-ol,
4-phenyl-3-butyn-1-ol, 4-phenyl-3-butyn-2-ol,
1-phenyl-3-ethyl-1-heptyn-3-ol, 1-phenyl-1-hexyn-3-ol,
6-phenyl-5-hexyn-3-ol, 3-phenyl-3-hydroxy-1-butyne,
1-phenyl-2-(1-hydroxycyclohexyl)acetylene, 1-phenyl-2-(1-hydroxycyclopentyl)acetylene, 1-phenyl-3-methyl-1-butyn-3-ol, 1-phenyl-3-methyl-1-pentyn-3-ol,
1-phenyl-4-methyl-1-pentyn-3-ol, 1-phenyl-1-pentyn-3-ol,
1-phenyl-2-propyn-1-ol, 3-phenyl-2-propyn-1-ol (phenyl propargyl alcohol), 3-phenyl-1-propyn-3-ol,
3-phenyl-1-butyn-3-ol, 1-butynyl-1-cyclohexanol,
1-butynyl-1-cyclopentanol, 1-ethynyl-1-cyclohexanol,
1-ethynyl-1-cyclopentanol,
1-phenyl-2-(1-hydroxycyclohexyl)acetylene,
1-phenyl-2-(1-hydroxycyclopentyl)acetylene,
1-propynyl-1-cyclohexanol, 1-propynyl-1-cyclopentanol,
3,6-diethyl-4-octyn-3,6-diol, 4,7-dimethyl-5-decyn-4,7-diol,
2,5-dimethyl-3-hexyn-2,5-diol, 3,6-dimethyl-4-octyn-3,6-diol,
3-hexyn-2,5-diol, 2,4,7,9-tetramethyl-5-decyn-4,7-diol,
acetylene dicarboxylic acid, 2-heptynoic acid,
2-hexynoic acid, 2-nonynoic acid, 2-octynoic acid,
2-pentynoic acid, 3-pentynoic acid, phenyl propiolic acid,
propiolic acid,
acetyl phenyl acetylene (1-phenyl-1-butyn-3-one),
3-butyn-2-one, 3-heptyn-2-one, 1-hexyn-3-one,
3-octyn-2-one, 1-pentyn-3-one, 4-pentyn-2-one,
2-butynediol diacetate, diethyl acetylene dicarboxylate,
ethyl-2-heptynoate,
ethyl-2-hexynoate, ethyl-2-octynoate,
ethyl-2-pentynoate,
propargyl acetate,
propargyl propionate, n-amyl propargyl ether,
n-butyl propargyl ether, t-butyl propargyl ether,
butynediol dimethyl ether, dipropargyl ether,
ethoxy acetylene, 1-ethoxy-1-butyne, 1-ethoxy-2-butyne,
1-ethoxy-2-heptyne, 1-ethoxy-1-hexyne, 1-ethoxy-2-hexyne,
1-ethoxy-2-octyne, 1-ethoxy-1-pentyne, 1-ethoxy-2-pentyne,
1-ethoxy-1-propyne, ethyl propargyl ether,
n-hexyl-propargyl ether, methoxy acetylene,
1-methoxy-1-buten-3-yne, 1-methoxy-2-butyne,
1-methoxy-2-heptyne, 1-methoxy-2-hexyne, 1-methoxy-2-octyne,
1-methoxy-2-pentyne, methyl propargyl ether,
phenyl propargyl ether,
methyl propiolate, ethyl propiolate, dimethyl acetylene-dicarboxylate, diisopropyl acetylenedicarboxylate,
ethyl phenylpropiolate, methyl 3-chlorophenylpropiolate,
ethyl 4-ethoxyphenylpropiolate, methyl 2-butynoate,
propyl 2-hexynoate, benzoylacetylene, 3-bromobenzoylacetylene,
4-ethylbenzoylacetylene, 3-butyn-2-one, and the like.

The 3-diazoindol-2(3H)-ones employed in the abovedescribed processes in general are prepared from the corresponding isatin compound. The preparation of isatin compounds is well known in the art. The required N-substituted isatin is obtained by either of two routes, depending upon whether the N-substituent is (1) alkyl or aralkyl, or (2) aryl. When the desired isatin nitrogen substituent is alkyl or aralkyl, the isatin compound is prepared by N-alkylation of the parent compound with an alkyl or aralkyl halide in the presence of a strong base such as, for example, sodium hydride. However, when an aryl substituent on the isatin nitrogen is desired, a different procedure must be employed. In that case, the desired N-aryl isatin is prepared directly by cyclization with oxalyl chloride of an appropriately-substituted diarylamine.

Once the desired isatin has been obtained, the corresponding 3-diazoindol-2(3H)-one is prepared in accordance with known procedures. See, for example, J. M. Michowski, Tetrahedron Letters, 1773 (1967) and M. P. Cava, et al., J. Am. Chem. Soc., 80, 2257 (1958). The appropriate isatin compound is treated with p-toluenesulfonylhydrazine. The resulting hydrazone then is treated with a base such as aqueous sodium hydroxide or aluminum oxide to give the desired 3-diazoindol-2(3H)-one.

The compounds of formula I of the invention wherein $R^1$ and/or $R^2$ are

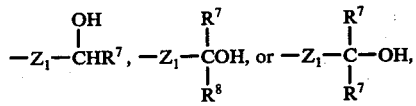

(wherein $R^4$ and $R^5$ are other than hydroxy, alkanoyloxy, or halogen), are also prepared by reacting compounds of formula V wherein $R_1^1$ and/or $R_1^2$ are

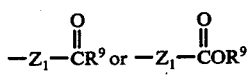

(wherein $R^9$ is other than hydrogen), with alkyl, phenylalkyl and phenyl Grignard reagents of the formula VI

wherein $X_2$ is Cl or Br and $R^9 \neq H$, or with alkyl, phenylalkyl and phenyl lithium reagents of the formula VII

wherein $R^9 \neq H$.

Compounds of formula V wherein $R_1^1$ and/or $R_1^2$, are —CH=O or

are prepared by selectively oxidizing compounds of formula V wherein $R_1^1$ and/or $R_1^2$ are methyl (or hydroxymethyl) with selective oxidizing agents such as chromyl chloride or chromic acid (or manganese dioxide), respectively, in essentially non-reactive solvents such as carbon disulfide or acetic acid-sulfuric acid mixtures, (or in chloroform) respectively.

Where the $R_1^1$ or $R_1^2$ groups represent

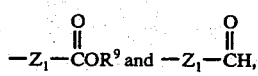

then the total number of carbons in the $Z_1$ group will be 3 or less. Where $R_1^1$ or

wherein $R^9$ is lower alkyl or

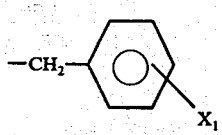

then the total number of carbon atoms in the

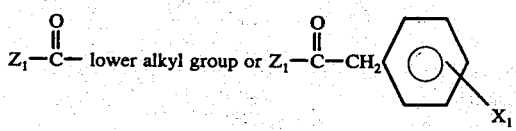

group will be 4 or less.

The reaction can be run in an inert aprotic organic solvent such as an ether like diethyl ether, tetrahydrofuran, or 1,2-dimethoxyethane at a temperature of $-70°$, or just above the freezing point of the reaction mixture, to 100° C for 0.5 to 72 hours. The products are isolated by cooling, neutralization with mild acid, and extraction.

Compounds of formula I wherein $R^1$ and/or $R^2$ are

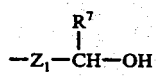

and where $R^4$ and/or $R^5 \neq$ alkanoyloxy are also prepared by several other methods. One general method involves selectively reducing (chemically or by catalytic means) the compounds of formula V wherein $R_1^1$ and/or $R_1^2$ are

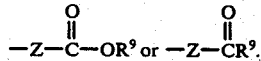

Exemplary of the chemical reduction processes is the reaction of a compound of formula V wherein $R_1^1$ and/or $R_1^2$ are

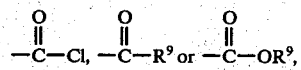

with metal hydrides, such as aluminum hydride; substituted metal hydrides, such as diisobutyl aluminum hydride; complex metal hydrides, such as magnesium aluminum hydride, sodium aluminum hydride, aluminum borohydride, calcium borohydride and the like, alkoxyaluminum hydrides, such as sodium di-(2-methoxyethoxy)-aluminum hydride and the like; and of compounds of formula VI wherein $R_1^1$ and/or $R_1^2$ are any of the above other than —COOH with complex metal hydrides, such as lithium borohydride or sodium dimethoxy borohydride; and wherein $R_1^1$ and $R_1^2$ are

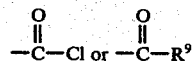

with complex metal hydrides, such as potassium borohydride and sodium borohydride, and mixtures of the above with magnesium and aluminum chlorides and bromides.

The reaction can be run in inert non-hydroxylic organic solvents, such as ether (4–12 carbons), for example, diethyl ether, diisopropyl ether, diphenyl ether, tetrahydrofuran, dioxane, 1,2-dimethoxyethane and the like; saturated hydrocarbons (6–10 carbons), such as n-hexane, cyclohexane; aromatic hydrocarbons (6–10 carbons), such as benzene, toluene, xylene; halogenated hydrocarbons (1–4 carbons), such as methylene chloride, chloroform, dichloroethane, tetrachloroethane; or, where compatible with the less reactive reducing agents, such as sodium borohydride, in alkanols (1–6 carbons) such as methanol, isopropanol or, preferably, ethanol, at a temperature of 25° C to reflux for 0.5 hour to 48 hours.

Other chemical reducing agents which can be used in the process of this invention include (wherein $R_1^1$ and/or $R_1^2$ are

aluminum and sodium alkoxides in the presence of the corresponding alcohol, e.g., aluminum isopropoxide in isopropanol; (wherein $R_1^1$ and/or $R_1^2$ are

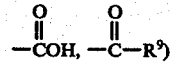

borane in inert non-hydroxylic solvents such as ethers like tetrahydrofuran; ethyl ether; (wherein $R_1^1$ and/or $R_1^2$ are

dialkylboranes such as di(1,2-dimethylpropyl)borane in inert non-hydroxylic solvents as above.

Compounds of formula I wherein $R^1$ and/or $R^2$ are $CH_2(CH_2)_nCH_2OH$ can also be prepared via a Willgerodt-Kindler reaction by reacting appropriate compounds of formula I, wherein $R^1$ and/or $R^2$ is

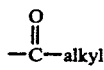

(wherein alkyl is of the formula $-(CH_2)_nCH_3$), with sulfur and ammonium hydroxide or sulfur with an amine, such as morpholine, or with ammonium polysulfide at from about 40° C to about 220° C, preferably 80° C to 180° C, for from 0.5 hour to about 48 hours, preferably 2 to 24 hours.

The product of formula V wherein $R_1^1$ and/or $R_1^2$ is the corresponding thioamide, e.g.,

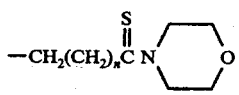

(from the reaction where $R_1^1$ and/or $R_1^2$ is

with sulfur and morpholine) is hydrolyzed in, for example, refluxing concentrated HCl to give the corresponding acid of formula I where $R^1$ and/or $R^2$ is $-CH_2(CH_2)_nCO_2H$.

Reduction of the above acid with a selective chemical reducing agent such as diborane in tetrahydrofuran gives the alcohol of formula V wherein $R^1$ and/or $R^2$ is $CH_2(CH_2)_nOH$.

Compounds of formula V wherein one of $R_1^1$ and $R_1^2$ is hydrogen; alkyl (1-3 carbons); phenyl; phenyl substituted with $X_1$ [that is alkyl (1 to 4 carbons), alkoxy (1 to 4 carbons)], benzyl; or benzyl substituted with $X_1$; and the other of $R_1^1$ and $R_1^2$ is

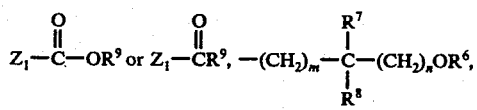

or where $R_1^1$ and $R_1^2$ are the same and are

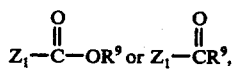

and where $R^6$ and $R^9 \neq H$, and where $R^4$ and $R^5 \neq OH$ are prepared by reacting compounds of the structure

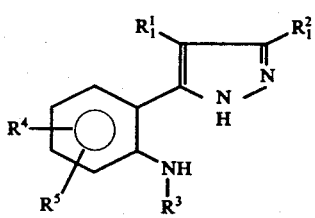

with phosgene in the presence of a base, such as alkali metal hydroxide, alkaline earth metal hydroxide or quaternary ammonium hydroxide or a heterocyclic amine, such as pyridine. The reaction is carried out in the presence of an inert organic solvent such as chlorinated hydrocarbons, for example methylene chloride or ethylene chloride, or aromatic hydrocarbons such as benzene, at temperatures ranging from about 0° C to reflux for periods of 0.5 to 48 hours.

Other cyclizing agents which may be employed in carrying out the above reaction include: 1,1'-carbonyldiimidazole in a halogenated aromatic solvent, e.g., o-dichlorobenzene, at 50° to reflux temperature, for 1 to 48 hours (preferably 1 to 24 hours); sodium hydride and 1-ethoxycarbonylimidazole in an ether, e.g., tetrahydrofuran, refluxed for 3 hours; urea at 200°, ethyl carbamate and $ZnCl_2$ at 190° (for 4 hours); and KNCO in acetic acid at 60° (for 6 hours).

Compounds of formula VIII where $R^3=H$ can be prepared by several methods such as from the corresponding nitro substituted compound

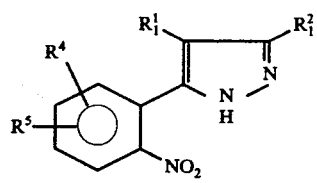

by employing conventional selective chemical reduction or catalytic hydrogen techniques, such as sodium sulfite, tin and HCl, zinc and acetic acid or hydrogen and Raney nickel, respectively.

The esters of formula V wherein $R_1^1$ and/or $R_1^2$ are $Z-CO_2R^9$ ($R^9 \neq H$) may be prepared from the corresponding carboxylic acids of formula V wherein $R_1^1$ and/or $R_1^2$ are $Z-COOH$ by known esterification procedures such as 1) alkylation of alkali metal or trialkylammonium salts of the acid with alkyl or aralkyl halides, e.g., methyl iodide, benzyl chloride; 2) alkylation of the carboxylic acid with diazoalkanes and diazoaralkanes, e.g., diazomethane; 3) conversion of the carboxylic acid to the corresponding acid chloride or acid bromide (e.g., by reaction of the above carboxylic acid salts with a slight excess of, for example, oxalyl chloride or thionyl chloride) and subsequent reaction with the appropriate alcohol, in the optional presence of a catalyst such as pyridine in e.g. methylene chloride.

Compounds of formula V wherein $R_1^1$ and/or $R_1^2$ are $-COOH$, and/or $R^3$ and/or $R^4$ and/or $R^5$ are OH are prepared by reacting compounds of formula V, wherein $R_1^1$ and/or $R_1^2$ are

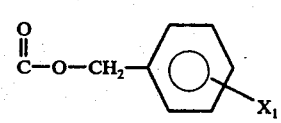

and/or $R^4$ and/or $R^5$ are

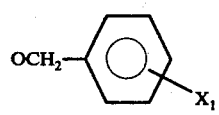

and $R^3$ is

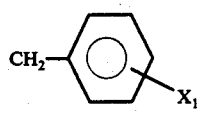

with an appropriate reducing agent under selective conditions in an inert organic solvent.

Typical reducing agents include a metal catalyst, preferably Raney nickel, and hydrogen in the optional presence of a hydrogen halide in an inert organic solvent. Typical solvents include alkanols of 1–6 carbons such as methanol, ethanol and the like. The preferred optional hydrogen halides are hydrogen chloride and hydrogen bromide. The reactions are carried out for from about 1/6 hour to about 92 hours, preferably for from about 1/2 to about 24 hours at from about −20° to about 100° C.

The last-mentioned compounds of formula V can also be prepared by reacting the last-mentioned starting materials of formula V with at least about 0.5, preferably at least about 0.8, molar equivalents of an inorganic hydrogen halide (preferably hydrogen chloride, hydrogen bromide and hydrogen fluoride) or with a halogenated alkyl carboxylic acid of 1–4 carbons, preferably trifluoroacetic acid. The reaction is run in anhydrous hydrogen fluoride, or, when employing other acids, in an optional inert solvent.

Typical solvents include alkyl carboxylic acids of 1–3 carbons, such as acetic acid and the like; ethers such as diethyl ether, dioxane, tetrahydrofuran and the like; alkanols of 1–6 carbons such as methanol, ethanol, and the like; alkyl esters wherein both the acid and the alcohol from which the ester is derived may have from 1–4 carbon atoms such as ethyl acetate, propyl acetate, ethyl propionate and the like; halogenated hydrocarbons such as methylene chloride, chloroform, di-, tri- and tetrachloroethanes and the like; nitroalkanes of 1–4 carbons such as nitromethane, nitroethane and the like; or alkyl ketones having alkyl radicals of 1–4 carbons such as acetone, methylethyl ketone and the like.

The reaction is carried out at from about −50° C to about 200° C, preferably from about 0° C to about 120° C, until a significant amount of end product is obtained, typically, for from about 1/10 to about 92, preferably from about 1/6 to about 30 hours. The product is isolated by conventional techniques. For example, with all acids except hydrogen fluoride, the reaction mixture is diluted with an inert water-immiscible organic solvent, washed with dilute aqueous sodium bicarbonate, dried and chromatographed. When using hydrogen fluoride, the hydrogen fluoride is evaporated, the residue dissolved in an inert organic solvent, such as halogenated hydrocarbons, e.g., methylene chloride, chloroform or trichloroethylene; alkyl esters wherein both the acid and the alcohol from which the ester is derived may have from 1–4 carbon atoms, e.g., ethyl acetate, propyl acetate, ethyl propionate and the like, washed with water, dried and chromatographed.

The compounds of formula V wherein $R_1^1$ and/or $R_1^2$ are $Z_1COOH$ and $R^4$ and $R^5$ are other than alkanoyl, and/or $R^4$ and/or $R^5$ are OH are also obtained by selectively hydrolyzing compounds of formula V, wherein $R_1^1$ and/or $R_1^2$ are $Z_1CO_2R^9$, and/or $R^4$ and/or $R^5$ are

(1–3 carbons) with from about 0.2 to about 6, preferably about 0.8 to about 3, molar equivalents of an alkali metal (preferably sodium and potassium) hydroxide, bicarbonate or carbonate in an optional inert organic solvent, in optional presence of water. Depending on the particular compound, care must be taken to minimize hydrolysis and cleavage of the quinazoline ring. Preferred conditions include absolute ethanolic potassium hydroxide. Suitable organic solvents include lower molecular weight alcohols, such as methanol, ethanol and the like; water-miscible ethers, such as tetrahydrofuran, 1,2-dimethoxyethane, dioxane and the like; N,N-dialkylformamides, N,N-dialkyl alkanoylamides wherein the alkyl and alkanoyl radicals have 1–4 carbons, such as dimethylformamide, dimethylacetamide, and the like. The reaction is carried out at from about −50° C to about 200° C, preferably about −20° C to about 70° C, for from about ¼ to about 72 hours, preferably about ½ to about 24 hours. The products are isolated in a conventional manner. For example, the reaction mixture is neutralized with acetic acid, evaporated and chromatographed.

Compounds of formula I wherein $R^4$ and/or $R^5$ are lower alkoxy are also prepared by reacting compounds of formula I wherein $R^4$ and/or $R^5$ are hydroxyl and where $R^3 \neq H$ or, if $R^3 = H$, the product may have $R^3$ = lower alkyl group of $R^4$ and/or $R^5$, with from about 0.5 to about 12, preferably from about 0.8 to about 3.0 molar equivalents of an appropriate base, e.g., $KHCO_3$, followed by reaction of the thus formed salt with a corresponding molar equivalent of an appropriate alkylating agent of formula lower alkyl-M wherein M is any group which is compatible with alkyl (1–3 carbons), and capable of being displaced by aryloxide anion under reaction conditions. Some typical M groups include halogen, preferably chlorine, bromine, iodine;

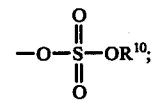

or an alkyl or arylsulfonate of formula

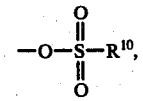

wherein $R^{10}$ can be alkyl of 1–6 carbons or aryl of from about 6 to 10 carbons optionally substituted by halogen, nitro or alkyl of 1–3 carbons. The reaction is run in an essentially inert organic solvent, e.g., lower alkyl ketones, such as methyl ethyl ketone.

Other typical bases include alkali metals (preferably lithium, sodium and potassium) and their salts of alkanols of 1–6 carbons such as methanol, ethanol, i-propanol, t-butyl alcohol, n-amyl alcohol and the like; of ammonia; of mono- and dialkylamines wherein the alkyl groups contain from 1–6 carbons such as ethylamine, diethylamine, di-isopropylamine, cyclohexyl isopropylamine and the like; of acidic hydrocarbons such as triphenylmethane and the like; thallous salts of the preceding alkanols; alkali metal (preferably sodium) hydrides.

Other typical organic solvents include alkanols of 1–5 carbons such as methanol, ethanol, t-butyl alcohol, n-butanol and the like; ethers of 4–12 carbons such as tetrahydrofuran, dioxane, diphenyl ether, 1,2-dimethoxyethane and the like; N,N-dialkylformamides, N,N-dialkylalkanoylamides wherein the alkyl and alkanoyl radicals have 1–4 carbons, such as dimethylformamide, dimethylacetamide and the like; dialkyl sulfoxides of 3–5 carbons such as dimethylsulfoxide and the like; hexamethylphosphorous triamide.

The reaction is carried out at from about −20° C to about 300° C, preferably from about 0° C to about 100° C for from about 0.2 hour to about 96 hours, preferably from about 0.5 hour to about 72 hours.

The products are isolated by conventional techniques. For example, the reaction mixture is refluxed for 5 hours, cooled, adjusted to pH 6 with aqueous HCl and evaporated; the residue is diluted with a water-immiscible, inert solvent such as methylene chloride, washed with water, dried and chromatographed.

In the above reaction when $R^3$ = H in the starting material, the resultant product has $R^3$ = lower alkyl.

Also, when $R^6$ = H in the starting material, appropriate conditions may be employed so that $R^6$ = H in the product. Such conditions include reacting the starting materials in a mixture of glyme and hexamethylphosphoric triamide at room temperature for 14 hours, followed by acidification with dilute aqueous hydrochloric acid and chromatography of the crude reaction extract. On the other hand, the corresponding product where $R^6$=lower alkyl can be obtained by employing other conditions such as using a large excess of the alkylating agent, elevated reaction temperatures and/or increased reaction times.

Compounds of formula V, wherein one of $R_1^1$ and $R_1^2$ is H but $R_1^1 \neq$ H when $R_1^2 = CO_2H$ are also prepared by decarboxylating compounds of formula V wherein one of $R^1$ and $R^2$ is carboxy in conventional manner, e.g., heating in the optional presence of a catalyst and/or organic solvent. Typical catalysts include: copper metal and salts, e.g., cuprous chloride. Typical solvents are: pyridine, butidine, quinoline, quinaldine; high-boiling ethers, e.g., diphenyl ether, di and triethylene glycol ethers.

The reaction is carried out from 50° C (or the freezing point of the run mixture) to 400° C (or the reflux temperature) for from 0.2 hour to 48 hours, or until the reaction is essentially complete.

Compounds of formula I wherein $R^4$ and $R^5$ are other than OH and $R^3$ is other than hydrogen or optionally substituted phenyl are also prepared by reacting compounds of formula I wherein $R^3$ is hydrogen with from about 0.5 to about 2, preferably from about 0.8 to about 1.3 molar equivalents of an appropriate base, followed by reaction of the thus formed salt with a corresponding molar equivalent of an appropiate alkylating agent of formula $R^3$-M wherein $R^3$ is other than hydrogen or optionally substituted phenyl and M is any group which is compatible with $R^3$ and capable of being displaced by the salt under the reaction conditions. Some typical M groups include halogen, preferably chlorine, bromine, iodine;

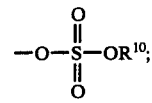

or an alkyl or arylsulfonate of formula

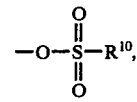

where $R^{10}$ can be alkyl of 1–6 carbons or aryl of from about 6 to 10 carbons optionally substituted by halogen, nitro or alkyl of 1–3 carbons. The reaction is run in an essentially inert organic solvent.

Typical bases include alkali metals (preferably lithium, sodium and potassium) and their salts of alkanols of 1–6 carbons such as methanol, ethanol, i-propanol, t-butyl alcohol, n-amyl alcohol and the like; of ammonia; of mono- and dialkylamines wherein the alkyl groups contain from 1–6 carbons such as ethylamine, diethylamine, di-isopropylamine, cyclohexyl isopropylamine and the like; of acidic hydrocarbons such as triphenylmethane and the like; thallous salts of the preceding alkanols, and, preferably, alkali metal hydrides such as sodium hydride.

Typical organic solvents include alkanols of 1–5 carbons such as methanol, ethanol, t-butyl alcohol, n-butanol and the like; ethers of 4–12 carbons such as tetrahydrofuran, dioxane, diphenyl ether, 1,2-dimethoxyethane and the like; N,N-dialkylformamides, N,N-dialkylalkanoylamides wherein the alkyl and alkanoyl radicals have 1–4 carbons, such as dimethylformamide, dimethylacetamide and the like; dialkyl sulfoxides, hexamethylphosphorous triamide and their mixtures.

The reaction is carried out at from about −20° C to about 300° C, preferably from about 0° C to about 100° C for from about 0.2 hour to about 96 hours, preferably from about 0.5 hour to about 72 hours.

The products are isolated by conventional techniques. For example, the reaction mixture is evaporated; the residue is neutralized with aqueous acid, extracted with a water-immiscible, inert solvent such as methylene chloride, washed with water, dried and chromatographed.

In the above reaction when $R^6$=H in the starting material, selective conditions must be employed to minimize alkylation of the hydroxyl at the 2-position so that $R^6$=H in the product. On the other hand, by using an excess of the alkylating agent, the corresponding product where $R^6$=lower alkyl can be obtained.

Compounds of formula I wherein $R^1$ and/or $R^2$ is Z—$OR^6$, where $R^6$ is lower alkanoyl, aralkanoyl, optionally substituted benzoyl are also prepared by reacting compounds of formula I wherein $R^1$ and/or $R^2$ is Z—$OR^6$ and $R^6$ is hydrogen with from about 0.8 to about 6, preferably from about 1 to about 3, molar equivalents of acyl derivatives of formula

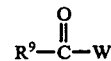

(where W is halogen, preferably chlorine and bromine, hydroxy, a radical of formula

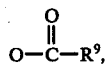

or a radical of formula

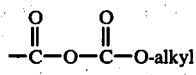

wherein alkyl has 1-6 carbons), in the optional presence of an appropriate base, in an optional, essentially inert organic solvent.

Typical suitable bases include heterocyclic amines of 5-10 carbons such as pyridine, 2-methylpyridine, 2,6-dimethylpyridine, quinoline, quinaldine and the like; trialkylamines wherein the alkyl radicals have 1-5 carbons, such as triethylamine, tributylamine and the like.

Typical inert organic solvents which may be used include aryl hydrocarbons such as benzene, toluene, xylene and the like; di-, tri- and tetra- chlorinated hydrocarbons such as trichloro and methylene chloride, chloroform, dichloro-, and tetrachloroethanes and the like; ethers such as 1,2-dimethoxyethane, tetrahydrofuran, dioxane and the like; N,N-dialkylformamides and alkyl alkanoylamides wherein the alkyl and alkanoyl radicals have 1-4 carbons such as dimethylformamide, dimethylacetamide and the like. In the preferred method, where W is hydroxy, no solvent is necessary and the reaction is carried out at the reflux temperature of the starting mixture, if liquid, or at the fusion point, if the starting mixture is a solid.

The reaction is carried out at from about 0° C to about reflux, preferably from about 20° C to about reflux, until a significant amount of end product is obtained, typically, for from 0.5 to about 80 hours, preferably from about 1 to about 24 hours.

The product is isolated by conventional techniques. For example, the reaction mixture is evaporated and diluted with a water-immiscible organic solvent such as chlorinated hydrocarbons, e.g., methylene chloride or chloroform and the like. The organic solution is washed with water, dried and chromatographed. In the above reaction when $R^4$ and/or $R^5$=OH in the starting materials, varying amounts of another product wherein $R^4$ and/or $R^5$ is the same, lower alkanoyl, aralkanoyl, optionally substituted benzoyl may be obtained.

It will be appreciated that the compounds of formula V described above may be converted to the formula I compounds of the invention by any of the chemical and/or catalytic reduction techniques or by employing appropriate Grignard or organometalic reagents described hereinbefore.

Starting materials or final products that are mixtures of isomers can be separated into the single isomers by methods in themselves known, e.g., by fractional distillation, crystallization and/or chromatography. Racemic products can likewise be resolved into the optical antipodes, for example by separation of diastereomeric salts thereof, e.g., of the fractional crystallization, in the case of basic compounds, of d- or l-tartrates, maleates, -mandelates, -N-acetylphenylalaninates or -camphor sulfonates, or, in the case of acid compounds, d- or l-α-methylbenzylamine and reconverting the diastereomeric salts into the free antipodes.

Certain of the compounds of formula I may form physiologically acceptable acid-addition salts or base addition salts with inorganic and organic acids or alkali metal or alkaline earth metal bases such as sodium hydroxide or calcium hydroxide. These salts frequently provide useful means for isolating the products from reaction mixtures by forming the salt in a medium in which it is insoluble. The free base may then be obtained by neutralization, e.g., with a base or acid. Then any other salt may again be formed from the free base and the appropriate inorganic acid or base. Illustrative are the hydrohalides, especially the hydrochloride and hydrobromide which are preferred, sulfate, nitrate, phosphate, oxalate, tartrate, maleate, fumarate, citrate, succinate, methanesulfonate, benzenesulfonate, toluenesulfonate, and the like.

The compounds of formula I, and their pharmaceutically acceptable salts, are useful in treating various allergic conditions in mammalian species such as mice, cats, dogs, etc., when administered in amounts ranging from about 1 milligram to about 500 milligrams per kilogram of body weight per day. The compounds can be used prophylactically or therapeutically to treat various allergic and immunological disorders and in particular to treat certain types of asthma, hay-fever, and rhinitis. A preferred dosage regimen would be from about 3 milligrams to about 200 milligrams per kilogram of body weight per day administered in a single dose or plurality of divided doses.

The compounds of formula I, and the pharmaceutically acceptable salts thereof, are anti-allergics which inhibit the effects of certain antigen-antibody reactions and in particular inhibit the release of mediators such as histamine. The anti-allergy activity of these compounds is determined by the reaginic antibody induced passive cutaneous anaphylaxis (PCA) reaction in rats. (See Bach, Immediate Hypersensitivity: Laboratory Models and Experimental Findings, Ann. Rep. Med. Chem., 7: 238-248 (1972), for a discussion of the predictability of clinical efficacy of compounds active in the PCA).

A compound of formula I, or a salt thereof, can be administered by the inhalation of an aerosol or powder as described in U.S. Pat. No. 3,772,336 (i.e., breathing finely divided particles of the active ingredient into the lungs), orally, or parenterally. Powders can be prepared by comminuting the active ingredient with a similarly comminuted diluent such as starch or lactose. Suitable forms for oral administration include capsules, tablets, and syrups, and a suitable form for parenteral administration is a sterile injectable. Such unit dosage forms are prepared by compounding with a conventional vehicle, excipients, binders, preservatives, stabilizers, flavoring agents or the like as called for by acceptable pharmaceutical practice. Also, the compounds of this invention can be formulated with other pharmaceutically active compounds such as bronchodilators, steroids, antihistamines, etc.

The compounds of the invention are also useful as antiinflammatory agents as determined by the reverse passive arthus test [Agents & Actions, 5, 39 (1975)] and are effective in the prevention and inhibition of granuloma formation in warm blooded animals, and may be used, for example, in a manner similar to phenylbutazone or indomethacin. They may be used to decrease joint swelling, tenderness, pain and stiffness in mammalian species, such as dogs and monkeys, e.g., in conditions such as rheumatoid arthritis.

Furthermore, the compounds of the invention are useful in mammals as inhibitors of 3',5'-cyclic adenosine phosphodiesterase and 3',5'-cyclic guanosine phosphodiesterase, as well as anxiolytic agents at a dosage level of from about 12 to about 100 mg/kg per day ip in one dose or in up to 4 divided doses; as inhibitors of platelet aggregation in vitro and therefore of potential use in the treatment of thrombosis.

The compounds of the present invention in the described dosages may be administered orally; however, other routes such as intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup of elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following Examples further illustrate and represent preferred embodiments of the invention. All temperatures are expressed in degrees Centigrade.

The following examples illustrate the present invention, without, however, limiting the same thereto. All temperatures are expressed in degrees Centigrade. The letter "(d)" following a melting point indicates at least some apparent decomposition was observed. The term "stripped" also means evaporation.

EXAMPLE 1

1-(Hydroxymethyl)-2-phenylpyrazolo[1,5-c]quinazolin-5(6H)-one

A.

5,6-Dihydro-5-oxo-1-phenylpyrazolo[1,5-c]-quinazolin-2-carboxaldehyde 4.8 g (0.030 mole) of 3-diazooxindole is suspended in 350 ml of benzene and 3.9 g (0.030 mole) of phenylpropargylaldehyde added. The reaction mixture is refluxed under nitrogen for 48 hours.

The reaction mixture is then stripped to a residue of 7.0 g. This is chromatographed on a 200 g-dry silica gel column which is eluted with 1.5 liters of chloroform/ether (3:2). From the eluates there is obtained 2.5 g (29%) of solid which is twice crystallized from chloroform/methanol (4:1) to give 1.67 g of analytically pure material, m.p. 347°–350° (d).

B.

1-(Hydroxymethyl)-2-phenylpyrazolo[1,5-c]-quinazolin-5(6H)-one

To a suspension of 4.0 g (0.0139 mole) of 5,6-dihydro-5-oxo-1-phenylpyrazolo[1,5-c]quinazolin-2-carboxaldehyde (prepared as in Example 1A) in 300 ml of methanol (at 0°) there is added 2.5 g (0.066mole) of sodium borohydride. The suspension is stirred at 0° for 15 minutes and then overnight at room temperature. Another 2.5 g of sodium borohydride is added, and, after 6 hours another 2.5 g, and stirring continued overnight. The reaction mixture is treated with 200 ml of water, the methanol stripped, the solid (3.7 g) filtered and dried. This material is suspended in 500 ml of absolute ethanol, the mixture cooled to 0°, treated with 2.5 g of sodium borohydride, and stirred for 5 hours at room temperature, after which reduction is complete. The suspension is treated with 250 ml of water and stripped to a low volume. The precipitate is filtered, washed with water and dried (wt. 2.5 g). Recrystallization from absolute ethanol containing 2% benzene gives 2.1 g of analytically pure material, which contains 1 mole of water, m.p. 267°–270° (d).

EXAMPLE 2

2-(Hydroxymethyl)pyrazolo[1,5-c]quinazolin-5(6H)-one

A.

5,6-Dihydro-5-oxopyrazolo[1.5-c]quinazoline-2-carboxylic acid, ethyl ester

A solution of 48 g (0.30 mole) of 3-diazooxindole and 38.7 g (0.39 mol) of ethyl propiolate in 2.1. of benzene is refluxed overnight. The reaction mixture is cooled to room temperature and the crude product filtered, wt.=60 g. Crystallization from absolute ethanol gives 54 g, m.p. 242°–244° (Sl. d.).

An analytical sample is prepared by taking a 10 g aliquot of the above material and recrystallizing three times with absolute ethanol, m.p. 253°–254° (Sl. d.), 3.9 g.

B.

2-(Hydroxymethyl)pyrazolo[1.5-c]quinazolin-5(6H)-one

A suspension of 3.84 g (0.015 mole) of 5,6-dihydro-5-oxopyrazolo[1.5-c]quinazoline-2-carboxylic acid ethyl ester prepared as described in part A above is stirred in 150 ml of tetrahydrofuran under nitrogen at room temperature. There is added 24 ml (0.034 mole) of a 20% solution of diisobutyl aluminum hydride in hexane. The resultant solution is stirred for 1 hour at room temperature whereupon 50 ml of methanol is added and the reaction mixture refluxed for 1 hour. The precipitate of aluminum alkoxide is filtered, air dried and Soxhlet extracted for 48 hours with boiling methanol. The extract is combined with the above filtrate and stripped to give 3.2 g of a white solid (quantitative yield). Recrystallization from methanol gives 2.7 g of pure title compound, m.p. 285°–287°.

EXAMPLE 3

2-(Hydroxymethyl)pyrazolo[1,5-c]quinazolin-5(6H)-one 1.28 g (0.005 mole) of 5,6-dihydro-5-oxopyrazolo-[1,5-c]quinazoline-2-carboxylic acid ethyl ester prepared as described in Example 2A is suspended in 100 ml of dichloromethane and treated with 7.9 ml (0.011 mole) of 20% di-isobutylaluminum hydride (Dibal). The resultant yellow solution is stirred at room temperature for 45 minutes, 2.0 ml (0.003 M) of Dibal solution is added and stirring continued for 17 hours.

An additional 2.0 ml (0.003 mole) of Dibal solution is added and the reaction stirred for 2 hours (total reaction time 20 hours). Approximately one-half of the reaction mixture is stripped to an oil, triturated and suspended in 150 ml of 1N hydrochloric acid. The solid is filtered off and dried to give 350 mg (65% direct yield) of product, m.p. 285°–287°.

EXAMPLE 4

2-(1-Hydroxyethyl)pyrazolo[1,5-c]quinazolin-5(6H)-one

A. 2-Acetylpyrazolo[1,5-c]quinazolin-5(6H)-one

A solution of 19.0 g (0.119 mole) of 3-diazooxindole and 10 g (0.147 mole) of 3-butyn-2-one in 800 ml of benzene is refluxed overnight. The reaction mixture is cooled to room temperature and the product filtered off (23.1 g). Recrystallization from methanol/chloroform gives 18.0 g of product with melting point 296°–299° (d). Further recrystallization from glacial acetic acid gives 14.2 g of pure product melting at 306°–308° (d).

B. 2-(1-Hydroxyethyl)pyrazolo[1,5-c]quinazolin-5(6H)-one

A suspension of 3.3 g (0.0146 mole) of acetylpyrazolo[1,5-c]quinazolin-5(6H)-one prepared as in part A above in 300 ml of absolute ethanol is cooled to 0° and 2.22 g (0.0584 mole) of sodium borohydride added. Stirring is continued at 0° for fifteen minutes and then at room temperature for 2 hours. The reaction mixture is treated with 150 ml of water, the solution stripped to about 100 ml, saturated with solid sodium chloride and adjusted to pH 6.0 (paper) with dilute (1N) hydrochloric acid. The resultant precipitate is filtered and dried to give 3.1 g of product (94%) melting at 242°–245°. Recrystallization from chloroform-methanol gives 3.0 g of the title compound, m.p. 250°–252°.

EXAMPLE 5

2-(1-Hydroxyethyl)-6-methylpyrazolo[1,5-c]quinazolin-5(6H)-one

A. 2-Acetyl-6-methylpyrazolo[1,5-c]quinazolin-5(6H)-one

To a solution of 5.0 g (0.0288 mole) of 1-methyl-3-diazooxindole in 200 ml of benzene there is added 2.38 g (0.035 mole) of 3-butyn-2-one and the solution refluxed overnight.

The reaction mixture is cooled to room temperature and the crude product filtered off and washed with ether to give 4.5 g, m.p. 250°–251°. Recrystallization from chloroform/methanol gives 4.0 g of pure product, m.p. 250°–251°.

B. 2-(1-Hydroxyethyl)-6-methylpyrazolo[1,5-c]-quinazolin-5(6H)-one 6.4 g (0.02669 mole) of 2-acetyl-6-methylpyrazolo-[1,5-c]quinazolin-5(6H)-one prepared as in part A above is suspended in 325 ml of methanol and chilled in an ice bath. Thereto is added (portions) 4.85 g (0.128 mole) of sodium borohydride. The mixture is stirred for 15 minutes in the ice bath, during which time a clear solution results, and then for 30 minutes at room temperature.

The solution is treated with 100 ml of water and the methanol stripped. The aqueous solution is extracted three times each with 100 ml of dichloromethane. The combined organic phases are washed twice with 75 ml each of saturated sodium chloride solution, dried with anhydrous sodium sulfate, and stripped to a foamy residue of 6.5 g (quantitative yield). This is covered with pentane and allowed to stand overnight at 5°. The tacky solid that has formed is filtered and dissolved in boiling acetone. Concentration of the solution on the steam bath and filtration on cooling gives 4.4 g of analytically pure title compound, m.p. 169°–172°.

EXAMPLE 6

2-(Hydroxyphenylmethyl)pyrazolo[1,5-c]quinazolin-5(6H)-one

A. Phenylethynyl ketone

A solution of 1-phenyl-2-propyne-1-ol (34.2 g) in 50 ml acetone is cooled down to 0°, stirred under $N_2$ and treated dropwise, over a period of 3 hours with a solution of chromium trioxide (17.5 g) in water (50 ml) and concentrated sulfuric acid (14.8 ml), keeping the temperature below 5° at all times. After the addition is complete, the mixture is stirred for another hour at 5°. The reaction mixture is then diluted with water (100 ml) and extracted with two 250-ml portions of ether. The organic extracts are combined, dried over anhydrous sodium sulfate, filtered and stripped to give a yellow product. A small amount dried on a porous plate gives a m.p. of 45°–47°.

B. 2-Benzoylpyrazolo[1,5-c]quinazolin-5(6H)-one 6.23 g (0.039 mole) of diazooxindole and 6.6 g (0.051 mole or 1.3 equiv) of the phenylethynyl ketone prepared as in part A above (dried on a porous plate before being weighed out) are suspended in benzene (275 ml) and the mixture is refluxed under $N_2$ for 19 hours. The reaction mixture is cooled and the precipitates that form are filtered off, washed well with anhydrous ether (150 ml) and dried in a vacuum oven at ~70° for 1-½ hours. Yield: 10.3 g, m.p. 308°–311°. Additional product of 400 mg is obtained on refluxing the filtrate for another 24 hours. Total crude yield: 94.4%.

The crude product is recrystallized by taking it up in 400 ml dimethylformamide, concentrating the solution down to 300 ml and pouring this onto 1.5 liters icewater. After stirring for 30 minutes, the beige precipitates are filtered off and dried at 80° C. Yield: 10.3 g, m.p. 312°–314°.

C. 2-(Hydroxyphenylmethyl)pyrazolo[1,5-c]quinazolin-5(6H)-one 1.65 g 80.0057 mole) of 2-benzoylpyrazolo[1,5-c]-quinazolin-5(6H)-one prepared as in part B above is stirred with 880 mg (4 equiv) of sodium borohydride in absolute ethanol (125 ml) at room temperature for 3 hours. The reaction mixture is stripped to dryness and the resulting solid is suspended in water (40 ml), cooled down to 0° and treated dropwise with 1 N HCl 25 ml). The mixture is stirred for 30 minutes, diluted with water (40 ml) and stirred for another 10 minutes. The white precipitates are filtered off, washed well with water and dried overnight in a vacuum oven at 70° C to give 1.6 g of product.

The crude product is combined with another 200 mg of material from a previous run and recrystallized by taking it up in 95% ethanol (100 ml), filtering while hot and concentrating the clear filtrate down to a volume of 25 ml. After cooling the precipitates are filtered off and washed with a few ml of 95% ethanol. The product is dried in a vacuum oven for 1-½ hours at 70°. Yield: 1.47 g, m.p. 231°-233°.

EXAMPLE 7

2-[(2-Hydroxypropyl)]-pyrazolo[1,5-c]quinazolin-5(6H)-one 3.09 g (0.011 mole) of 5,6-dihydro-5-oxopyrazolo-[1,5-c]quinazolin-5(6H)-2-carboxylic acid ethyl ester prepared as in Example 2A is suspended in dry distilled tetrahydrofuran (60 ml), the system flushed with argon and the suspension rapidly treated with 3.6 ml (1 equivalent) of 3.13 M $CH_3MgCl$. The mixture is stirred for 5 hours after which 9.6 ml (2.5 equivalents) of the above Grignard reagent is rapidly added. (Solution occurs within 5 minutes.) The reaction mixture is stirred at room temperature for 30 minutes and then refluxed for 30 minutes. The mixture is cooled down to room temperature. 4 ml of saturated $NH_4Cl$ solution is added and the mixture is stirred for 10 minutes. The salts that form are filtered off and washed well with another 60 ml of tetrahydrofuran. The filtrate and washings are combined and stripped to dryness. Yield: 2.2 g, 82% crude yield. The resulting product is taken up in a mixture of ethyl acetate (100 ml) and absolute ethanol (25 ml); the solution is filtered while hot and the clear filtrate is concentrated down to a volume of ~50 ml on the steam bath. The precipitates that form on cooling are filtered off and washed with a few ml of ethyl acetate. Drying overnight in a vacuum oven at ~75° yields 950 mg of title compound, m.p. 228°-229°.

EXAMPLE 8

2[1-Hydroxy-1-phenylethyl)-pyrazolo[1,5-c]quinazolin-5(6H)-one 5.0 g (0.022 mole) of the methyl ketone 2acetyl-pyrazolo[1,5-c]quinazolin-5(6H)-one prepared as in Example 4A is suspended under argon in dry distilled tetrahydrofuran (100 ml) and treated quickly with 7.0 ml (~1.0 equivalent) of 3M $C_6H_5MgBr$/ethyl ether. The mixture is stirred for 5 minutes and another 15 ml (~2 equivalents) of the Grignard reagent is quickly added. The reaction mixture (dark brown) is stirred at room temperature for 30 minutes and then refluxed for another 30 minutes, cooled down to room temperature and the resulting reddish solution is treated with 8.0 ml of saturated $NH_4Cl$ solution. The mixture is diluted with 70 ml tetrahydrofuran and stirred at room temperature for ~1 hour. The inorganic salts are filtered off and washed well with tetrahydrofuran (30 ml) and $CHCl_3$ (50 ml). The filtrates are combined and stripped to dryness. Yield: 8.4 g; 3 spots on TLC.

The crude product is impregnated onto silica gel and chromatographed on a silica gel column (100 ml). The column is eluted successively with chloroform (750 ml). $CHCl_3$:ethyl acetate (1:1, 1.0 l.) and ethyl acetate (750 ml). The fractions containing both starting material and product are combined and stripped to dryness. Yield: 7.0 g. Fractional crystallization of this mixture from ethyl acetate gives 1.45 g of pure product, m.p. 213°-214°.

EXAMPLE 9

1,2-Bis(hydroxymethyl)pyrazolo[1,5-c]quinazolin-5(6H)-one

A.

5,6-Dihydro-5-oxopyrazolo[1,5-c]quinazoline-1,2-dicarboxylic acid, dimethyl ester A solution of 4.8 g (0.03 mole) of 3-diazooxindole in 150 ml of warm (45°) benzene is treated with 5.10 g (0.036 mole) of dimethylacetylene dicarboxylate. After stirring for 6 hours at 45°, an additional 0.426 g (0.003 mole) of ester is added and reaction continued overnight.

The precipitate that forms is filtered off and dried, 5.6 g, m.p. 242°-244° (d). This material is crystallized from ethyl acetate to give 3.46 g of the title compound, m.p. 250°-252° (d).

B.

1,2-Bis(hydroxymethyl)pyrazolo[1,5-c]quinazolin5(6H)-one 5.0 g (0.0165 mole) of 5,6-dihydro-5-oxopyrazolo[1,5-c]-quinazoline-1,2-dicarboxylic acid, dimethyl ester prepared as in part A is suspended in distilled dry tetrahydrofuran (100 ml), and treated with 1.69 g (0.066 mole or 4 equivalents) of 85% $LiBH_4$ at room temperature. The reaction mixture is stirred for 24 hours under $N_2$, cooled down to 0° C and treated dropwise with 1.0 N HCl (70 ml). The suspension is stirred for 30 minutes, diluted with 100 ml $H_2O$ and stirred for another 10 minutes. The white precipitates are filtered off, washed well with water and dried overnight in a vacuum oven at room temperature. Yield: 4.1 g, of crude product, m.p. 247°-250°; quantitative crude yield.

The crude product is taken up in 800 ml $CH_3OH$ and 150 ml $CHCL_3$ and the resulting solution concentrated down to 450 ml and filtered while hot. The clear filtrate is cooled and the white needles that form are filtered off and dried in a vacuum oven at 70° for 24 hours to give 3.17 g of title compound, m.p. 250°-251°.

EXAMPLE 10

2-[(Acetyloxy)methyl]pyrazolo[1,5-c]quinazolin-5(6H)-one

Three grams (0.014 mole) of the product of Example 3 [2-(Hydroxymethyl)pyrazolo[1,5-c]quinazolin-5(6H)-one] is refluxed with 250 ml of glacial acetic acid for 20 hours under nitrogen. The solution is cooled and stripped to a solid residue which is dissolved in a mixture of ethyl acetate-absolute ethanol. The volume of solution is reduced and the concentrated solution set aside at 5°. The precipitate is filtered off to give 3.5 g of product. Recrystallization from ethyl acetate-absolute ethanol gives 3.1 g of analytically pure title compound, m.p. 177°-179°.

EXAMPLE 11

2-(2-Hydroxyethyl)pyrazolo[1,5-c]quinazolin-5(6H)-one

A.

2-[2-(4-Morpholinyl)-2-thioxoethyl]pyrazolo[1,5-c]quinazolin-5(6H)-one 4.0 g (0.018 mole) of acetylpyrazolo[1,5-c]quinazolin-5(6H)-one, 1.41 sulfur and 3.1 g of morpholine are mixed well and heated in an oil bath at 150° for 3 hours. The mixture is cooled and the solid obtained is washed successively with water (50 ml), 6N HCl (50 ml) and water (150 ml). The solid material is then taken up in 1.4 liters absolute ethanol and 300 ml of chloroform, heated to boiling until a clear solution is obtained and treated with activated carbon for ~10 minutes. The suspension is filtered through a celite pad, while washing the pad well with 100 ml boiling ethanol. The filtrate is then concentrated down to a volume of ~800 ml, cooled; the light yellow precipitates that form are filtered off and dried in a vacuum oven at 60° C for 2-½ hours to give 3.8 g of product, m.p. 273–275°. Percent yield: 67.1% (recrystallized).

B.

5,6-Dihydro-5-oxopyrazolo[1,5-c]quinazoline-2-acetic acid 4.0 g (0.012 mole) of 2-[2-(4-morpholinyl)-2-thioxoethyl]pyrazolo-[1,5-c]quinazolin-5(6H)-one (prepared as in part A) is refluxed in concentrated hydrochloric acid (80 ml) for 4 hours and cooled. The precipitates are filtered off, washed well with water and dried in a vacuum oven at 80° for 3 hours. Yield: 2.84 g, 96% crude yield. The crude product is taken up in methanol (1.1 liters) and chloroform (300 ml), heated to boiling and the clear solution treated with activated carbon for ~10 minutes. The hot suspension is filtered through a celite pad and the clear filtrate is concentrated down to a volume of ~400 ml on a steam bath. After cooling, the light yellow precipitates are filtered off and dried in a vacuum oven at 60° C for 4 hours to give 1.97 g of product, m.p. 253°–254°.

C.

2-(2-Hydroxyethyl)pyrazolo[1,5-c]quinazolin-5(6H)-one 2.0 g of the acid of part B (0.0082 mole) is taken up in 50 ml distilled tetrahydrofuran and treated dropwise with 11 ml (0.011 mole or 1.34 equivalents) 1 M BH₃ at 0°. The mixture is stirred for 2 hours at room temperature and stripped to dryness. The solid is suspended in 50 ml water, treated dropwise with 20 ml 1 N HCl, stirred for 45 minutes and filtered to yield ~800 mg of product (after drying in a vacuum oven at ~80° for 4 hours). The crude product is taken up in 20 ml tetrahydrofuran and treated with 15 ml (0.015 mole or 0.2075 g or 5 equivalents) of 1 M Bh₃ and stirred for ca. 65 hours. The reaction is filtered and the filtrate evaporated to dryness to give the title compound.

EXAMPLE 12

2-(Hydroxymethyl)-6-methylpyrazolo[1,5-c]quinazolin-5(6H)-one

A suspension of 5.35 g (0.025 mole) of 2-(hydroxymethyl)-pyrazolo[1,5-c]quinazolin-5(6H)-one (the product of Example 2) in 250 ml of dimethoxyethane (DME) is treated with 690 mg (0.029 mole) of oil-free sodium hydride followed by the addition of a solution of 3.3 ml (0.053 mole) of methyl iodide in 20 ml of hexamethylphosphoramide (HMPA). After stirring for 1 hour, 6.6 ml (0.106 mole) of methyl iodide is added and the suspension stirred overnight.

The reaction mixture is stirred into 200 ml of 1N aqueous hydrochloric acid and 400 ml of dichloromethane added. The organic phase is separated and washed successively with water, aqueous sodium thiosulfate solution, finally with water and stripped to a solid (6 g). Purification is effected by preparative TLC utilized Merck silica gel and methanol (9:1). The desired product is eluted from the adsorbent with dichloromethane-methanol (4:1) to give 1.1 g (19% direct yield) of the title compound. Recrystallization from methanol gives the analytical sample (945 mg), m.p. 183°–184°.

EXAMPLE 13

2-(methoxymethyl)-6-methylpyrazolo[1,5-c]quinazolin-5(6H)-one

To a suspension of 32 mg (0.0013 mole) of oil-free sodium hydride in 25 ml of glyme is added 227 mg (0.001 mole) of 2-(hydroxymethyl)-6-methylpyrazolo[1,5-c]quinazolin-5(6H)-one. The suspension is stirred for 15 minutes and then a solution of 0.66 ml (0.0107 mole) of methyl iodide in 2 ml of hexamethylphosphoric triamide added. The reaction mixture is stirred for 18 hours at room temperature. The solution is filtered and the filtrate stripped to an oil which is partitioned between dichloromethane and aqueous sodium thiosulfate. The organic phase is washed with water and stripped to an oil which is dissolved in acetone and applied to a Merck silica gel plate (20 cm × 20 cm × 2 mm thick). The chromatogram is developed with chloroform-methanol (9:1) and the product is eluted off with acetone. Evaporation of the acetone gives an oil that solidifies on standing under pentane at 5°. The yield of title compound is 100 mg (41%), m.p. 98°–100°.

EXAMPLE 14

2-(Formyloxymethyl)pyrazolo[1,5-c]quinazolin-5(6H)-one 2-(Hydroxymethyl)pyrazolo[1,5-C]quinazolin-5(6H)-one (3.3 g, 0.0153 mole) is suspended in 250 ml of 97–100% formic acid and refluxed overnight under nitrogen. The solution is stripped to dryness and the solid is recrystallized from dioxane to give 2.8 g (75% yield) of analytically pure title compound, m.p. 190°–192°.

EXAMPLE 15

2-(Propionyloxymethyl)pyrazolo[1,5-c]quinazolin-5(6H)-one 2-(Hydroxymethyl)pyrazolo[1,5-c]quinazolin-5(6H)-one 83.0 g, 0.0139 mole) is suspended in 250 ml of propionic acid and the mixture refluxed overnight under nitrogen. The resultant solution is stripped to a solid and recrystallized from absolute ethanol to give 2.6 g(69% yield) of analytically pure title compound, m.p. 184°–186°.

EXAMPLE 16

2-(n-Butyloxymethyl)pyrazolo[1,5-c]quinazolin-5(6H)-one 2-(Hydroxymethyl)pyrazolo[1,5-c]quinazolin-5(6H)-one (3.0 g, 0.0139 mole) is suspended in 250 ml of n-butyric acid and refluxed overnight under nitrogen. The resultant solution is stripped to a solid which is crystallized from a mixture of ethyl acetate-absolute ethanol to give 2.8 g of product (71% yield), m.p. 170°–172°. An analytical sample is prepared by recrystallizing the above material from ethyl acetate-absolute ethanol (1:4) to give 2.5 g of pure title compound, m.p. 170°–172°.

EXAMPLE 17

2-(Benzoylozymethyl)pyrazolo[1,5-c]quinazolin-5(6H)-one

A mixture of 3.0 g (0.014 mole) of 2-(hydroxymethyl)-pyrazolo[1,5-c]quinazolin-5(6H)-one and 100 g of benzoic acid is heated at the point of fusion (140°–145°, silicone oil bath) under nitrogen for 18 hours (using a magnetic stirrer for agitation). The melt is poured into a well stirred solution of 1 molar sodium bicarbonate, the insoluble solid filtered, washed with water and dried to give (3.8 g, 85%) of the title compound, m.p. 262°–265°. An analytical sample is prepared by recrystallizing 0.5 g of this material from dioxane-isopropyl ether, m.p. 270°–272°.

EXAMPLE 18

10-Chloro-7-methoxy-2-(hydroxymethyl)pyrazolo[1,5-c]-quinazolin-5(6H)-one

A.
4-Chloro-7-methoxy-isatin-3-p-toluenesulfonylhydrazone 25.0 g (0.118 mole) of 4-chloro-7-methoxyisatin is taken up in 500 ml CH$_3$OH at 60° and treated portionwise with 23.8 g of 97% p-toluenesulfonylhydrazine ($\simeq$ 23.1 g or 1.05 equivalents). The mixture is kept at ~60° for 15 minutes and then stirred at room temperature for 20 hours.

The reaction mixture is concentrated to one half its original volume and filtered, and dried in vacuo for 1 hour to yield 37.6 g, m.p. 210°–211°, 85% crude yield (theor. yield = 44.2 g). The crude material is taken up in 1.0 l. dioxane and the dark-red solution concentrated down to 400 ml and cooled. The resulting yellow precipitates are dried overnight in vacuo at ~70° to give 27.73 g of product, m.p. 217°–218°. The filtrate is concentrated to a volume of 200 ml and cooled. The precipitates are filtered off and dried. Yield: 4.4 g of product, m.p. 213°–214°.

B. 4-Chloro-7-methoxy-3-diazooxindole 30.0 g (0.079 mole) of the isatin-3-p-toluenesulfonylhydrazone (prepared in part A) is suspended in 900 ml 0.2 N NaOH and heated slightly for ~30 minutes. The mixture is stirred for 22 hours at room temperature with a layer of methylene chloride (300 ml). The methylene chloride is stripped off and the aqueous phase saturated with CO$_2$ (dry ice used). The light peach-colored precipitates are filtered off, washed with a small amount of H$_2$O and dried in vacuo at 45° for 1½ hours to give 19.2 g of title compound (Theor. yield = 17.7 g). The crude product is taken up in 1.8 l. CH$_3$OH and the clear light red solution concentrated down to a volume of 500 ml, cooled, filtered and dried overnight in vacuo at room temperature. Yield of title compound is 15.2 g, m.p. 206°–207°, light orange crystals.

C.
10-Chloro-7-methoxy-2-(hydroxymethyl)pyrazolo-[1,5-c]quinazolin-5(6H)-one 2.0 g (0.0089 mole) of the 4-chloro-7-methoxy-3-diazooxindole (prepared in part B) and 10.3 g of 97% propargyl alcohol are refluxed under argon for 4 hours and cooled. The reaction mixture is diluted with 200 ml of ethyl ether and stirred for ~20 minutes and cream-colored precipitates are filtered off. Yield: 2.53 g, m.p. 221°–222°; quantitative crude yield (theor.: 2.49 g). This crude product is taken up in 200 ml absolute ethanol, the clear solution filtered while hot and the filtrate concentrated down to a volume of 50 ml and cooled. The resulting precipitates are filtered off and dried in vacuo at 45° over the weekend to give 1.59 g of title compound, m.p. 230°–232°.

EXAMPLE 19

9-Chloro-2-(Hydroxymethyl)pyrazolo[1,5-c]quinazolin-5(6H)-one 2g of 5-chloro-diazooxindole (0.01033 mole) and 13 ml ($\simeq$0.22 mole or 21.5 equivalents) of propargyl alcohol are refluxed under N$_2$ for 4.5 hours and cooled. The mixture is diluted with 200 ml ethyl ether, and stirred for 18 30 minutes. The resulting precipitates are filtered off and washed well with ethyl ether to yield 2.41 g of crude product, 93.4% crude yield.

The crude product is taken up in 800 ml absolute ethanol and 300 ml CHCl$_3$, treated with activated carbon, for ~10 minutes while hot, filtered through a celite pad and the clear filtrate concentrated down to a volume of ~300 ml and cooled. The white precipitates that form are filtered off to give 1.0 g of title compound, m.p. 316°–318°. The filtrate is concentrated down further to a volume of 150 ml and cooled to give another 310 mg of product, m.p. 311°–313°.

EXAMPLE 20

2-(Hydroxymethyl)pyrazolo[1,5-c]quinazolin-5(6H)-one 500 mg (0.0019 mole) of 5,6-dihydro-5-oxopyrazolo[1,5-c]quinazoline-2-carboxylic acid, ethyl ester, prepared as described in Example 2A, is suspended in 10 ml distilled tetrahydrofuran and treated with 99.6 mg (0.0039 mole or 2 equivalents) of 85% lithium borohydride at room temperature. The mixture is stirred overnight (~20 hours), cooled down to 0° C, treated with 4.5 ml of 1.0 N hydrochloric acid and stirred for 30 minutes. The mixture is then diluted with water (25 ml), stirred for 10 minutes and filtered. The white precipitates are dried in a vacuum oven at ~70° for 1.5 hours to give 344 mg of title compound, m.p. 289°–290°; 84% yield. An additional 31.3 mg is obtained from the filtrate on addition of an equal volume of methylene chloride.

EXAMPLE 21

2-(1-Hydroxycyclohexyl)pyrazolo[1,5-c]quinazolin-5(6H)-one 1.6 g (0.01 mole) of 3-diazooxindole and 12.4 g (0.1 mole) of ethynylcyclohexanol are refluxed under N$_2$ for 4.5 hours.

The cooled mixture is diluted with 50 ml ethyl ether, stirred for 20 minutes and the precipitates filtered off and washed well with ethyl ether to give 2.22 g of product, m.p. 249°–251°.

The crude product is taken up in 150 ml absolute ethanol, filtered while hot and the clear filtrate concentrated down to a volume of ~50 ml and cooled. The precipitates are filtered off to yield 1.65 g of title compound, m.p. 253°–254°.

EXAMPLE 22

2-(Hydroxymethyl)pyrazolo[1,5-c]quinazolin-5(6H)-one 2.0 g (0.0126 mole) of 3-diazooxindole is dissolved in 22 ml of propargyl alcohol (0.378 mole) and refluxed under nitrogen for 3 hours. The reaction mixture is cooled to room temperature and diluted with 10 volumes of ethyl ether. The solid is filtered, washed with ethyl ether and dried to give 2.0 of product (75% direct yield). Recrystallization from methanol gives 1.5 g of title compound, m.p. 286°–288° (sl. dec.).

EXAMPLE 23

2-(Hydroxymethyl)pyrazolo[1,5-c]quinazolin-5(6H)-one 4.8 g (0.03 mole) of 3-diazooxindole is suspended in 500 ml of benzene and 1.96 g (0.033 mole) of propargyl alcohol added. The reaction mixture is refluxed overnight under nitrogen, after which 19.6 g (0.33 mole) of propargyl alcohol is added and the reaction continued under reflux for a total of 48 hours. The tan solid which precipitates is filtered off (1.5 g, 23% yield), m.p. 272°–275° (sl. dec.). Recrystallization from methanol gives crystals of the title compound, m.p. 286°–288° (sl. dec.).

EXAMPLE 24

9-Chloro-2-[(acetyloxy)methyl]pyrazolo[1,5-c]quinazolin-5(6H)-one 2.50 g (0.01 mole) of 9-chloro-2-(hydroxymethyl)-pyrazolo-[1,5-c]quinazolin-5(6H)-one and 1.02 g of acetic anhydride in 50 ml pyridine are stirred for 12 hours then refluxed for 30 minutes. The reaction is evaporated; the residue is taken up in chloroform, washed with dilute aqueous sodium bicarbonate, with water and dried. The solvent is evaporated to give the title compound.

EXAMPLE 25

1-Methylpyrazolo[1,5-c]quinazolin-5(6H)-one-2-carboxylic acid

A suspension of 25.7 g (0.10 mole) of 1-methyl-pyrazolo-[1,5-c]quinazolin-5(6H)-one-2-carboxylic acid ethyl ester in 2.5 l of 10% alcoholic potassium hydroxide is refluxed for 3 hours, cooled to room temperature and filtered. The solid is dissolved in water extracted with chloroform, treated with Norit-A and filtered. The filtrate is cooled in an ice bath and acidified (Congo red) with 25 ml of concentrated hydrochloric acid. The white precipitate is filtered, digested with 1 l. of hot water and filtered, and dried to give the title compound.

EXAMPLE 26

1-Methyl-pyrazolo[1,5-c]quinazolin-5(6H)-one

Twelve grams of 1-methylpyrazolo[1,5-c]quinazolin-5(6H)-one-2-carboxylic acid is put into a 250 ml single neck round bottom flask, and stirred with a magnetic stirrer under a nitrogen atmosphere. The flask and contents are immersed in a silicone oil bath which is then heated to 285°. After 0.5 hour, the melt is removed from the bath and allowed to solidify. The crude solid is then pulverized and purified by high vacuum sublimation. The sublimate is recrystallized from methanol to give the title compound.

EXAMPLE 27

Pyrazolo[1,5-c]quinazolin-5(6H)-one-1-carboxylic acid

To 40 g (0.19 mole) of 1-methyl-pyrazolo[1,5-c]quinazolin-5(6H)-one in a rapidly stirring mixture of 350 g of concentrated sulfuric acid and 100 g of acetic acid is added, dropwise a solution of 100 g of chromic acid in 175 g water and 50 g acetic acid. After 12 hours, the reaction is poured into 2 l. of ice water. The reaction mixture is concentrated, cooled and the title compound filtered off and dried.

EXAMPLE 28

Pyrazolo[1,5-c]quinazolin-5(6H)-one-1-carboxaldehyde

To 16.1 g (0.021 mole) of 1-methyl-pyrazolo[1,5-c]-quinazolin-5(6H)-one in 125 g of carbon disulfide is added, over an 8 hour period, a solution of 31 g of chromyl chloride in 200 g of carbon disulfide. The temperature of the reaction mixture is kept below 47° with cooling. After 12 hours, the reaction mixture is concentrated, cooled and the title compound filtered off.

EXAMPLE 29

5,6-Dihydro-5-oxopyrazolo[1,5-c]quinazoline-2-($\alpha$,$\alpha'$-dimethyl)-acetic acid A solution of sodium amide (0.226 mole) in liquid ammonia is prepared in a 1 l. three-necked flask equipped with a condenser, a ball-sealed mechanical stirrer, and a dropping funnel. Commercial anhydrous liquid ammonia (500 ml) is introduced from a cylinder through an inlet tube. To the stirred ammonia is added a small piece of sodium. After the appearance of a blue color, a few crystals of ferric nitrate hydrate (about 0.25 g) are added, followed by small pieces of freshly cut sodium until 5.2 g has been added. After all the sodium has been converted to the amide 15.8 g (ca. 0.066 mole) of 5,6-dihydro-5-oxopyrazolo[1,5-c]quinazoline-2-acetic acid is added and the suspension is stirred for 15 minutes. To the suspension is added rapidly 93 g (0.066 mole) of methyl iodide in 25 ml of anhydrous ether, and the mixture is then stirred for 1 hour. The mixture is then evaporated to near dryness on a steam bath, 200 ml of ether added, and evaporation to dryness effected. Another 200 ml of ether is added, followed by evaporation to dryness. The resulting solid is then dissolved in 300 ml of water and washed with three 200 ml portions of ether. The aqueous solution is filtered through a layer of Celite to remove the slight brown coloration, and the filtrate is acidified with hydrochloric acid. The precipitate is collected by filtration and washed with three 100 ml portions of hot water and dried to give the title compound.

EXAMPLE 30 n-Butyl ester of 5,6-dihydro-5-oxopyrazolo[1,5-c]quinazoline-2-carboxylic acid

A.
5,6-Dihydro-5-oxopyrazolo[1,5-c]quinazoline-2-carboxylic acid, sodium salt 5,6-Dihydro-5-oxopyrazolo[1,5-c]quinazoline-2-carboxylic acid (4.58 g, 0.02 mole) is suspended in 300 ml of water and treated with 1.68 g (0.02 mole) of solid sodium bicarbonate. The mixture is stirred for 0.5 hour during which time almost complete solution results. The water is stripped to a low volume and 400 ml of acetone added. The white solid is filtered, washed with acetone and then ether to give 4.8 g of product.

B.
5,6-dihydro-5-oxopyrazolo[1,5-c]quinazoline-2-carbonyl chloride 4.8 g (0.019 mole) of 5,6-dihydro-5-oxopyrazolo[1,5-c]-quinazoline-2-carboxylic acid, sodium salt is added to a solution of 3.27 g (0.026 mole) of oxalyl chloride in 200 ml of benzene. The suspension is stirred at room temperature for 20 minutes and then refluxed under nitrogen for 2 hours. The solvent is stripped to give the product.

C.
5,6-Dihydro-5-oxopyrazolo[1,5-c]quinazoline-2-carboxylic acid, n-butyl ester To a suspension of 4.6 g (0.019 mole) of 5,6-dihydro-5-oxopyrazolo[1,5-c]quinazoline-2-carbonyl chloride in 200 ml of pyridine under nitrogen is added, slowly in a dropwise fashion, a solution of 1.98 g (0.019 mole) of n-butanol. After stirring overnight at room temperature, the reaction mixture is filtered and the filtrate concentrated to a small volume and diluted with cold water. The title compound is filtered off and dried, m.p. 198°–200°.

EXAMPLE 31

Dimethylethynylcarbinol acetate 112 g (one mole) of freshly distilled dimethylethynyl carbinol is treated with 1.2 moles of acetic anhydride containing 10 drops of 85% phosphoric acid. The acetic anhydride is added to the carbinol dropwise with shaking while maintaining the temperature under 40°. The mixture is allowed to stand overnight, washed with two 75 ml portions of cold water, and the water washings are extracted with ether. The ether extract is added to the main portion of ester and the combined ethereal solution is washed with 10% sodium carbonate solution until the washings remain basic to litmus. The solution is washed with two 75 ml portions of ice-water, dried over calcium chloride, and distilled to give the title compound.

EXAMPLE 32

2-(Hydroxymethyl)-6-(p-methoxybenzyl)pyrazolo[1,5-c]quinazolin-5(6H)-one 210 g of p-methoxybenzyl bromide and 40 g of potassium iodide are added to 114 g of 2-(hydroxymethyl)-pyrazolo[1,5-c]-quinazolin-5(6H)-one and 276 g of potassium carbonate in 2 l. of methanol. After refluxing for 5 hours, the reaction is cooled, poured into 6 l. of water and the title compound is filtered off and dried.

EXAMPLE 33

2-(Methoxymethyl)-6-(p-methoxybenzyl)pyrazolo[1,5-c]quinazolin-5(6H)-one

Following the procedure of Example 13, but substituting 2-(hydroxymethyl)-6-(p-methoxybenzyl)-pyrazolo[1,5-c]quinazolin-5(6H)-one for 2-(hydroxymethyl)-6-methyl-pyrazolo[1,5-c]-quinazolin-5(6H)-one in Example 13 gives the title compound.

EXAMPLE 34

2-(Methoxymethyl)pyrazolo[1,5-c]quinazolin-5(6H)-one 2.9 g (0.01 mole) of 2-(methoxymethyl)-6-(p-methoxybenzyl)pyrazolo[1,5-c]quinazolin-5(6H)-one in 100 ml of anhydrous hydrogen fluoride is stirred at 20° C for one hour. The hydrogen fluoride is then evaporated; the residue is partitioned between methylene chloride and dilute aqueous sodium bicarbonate. The organic phase is washed with water, dried and evaporated. The residue is stirred with ether and the title compound is filtered off and dried.

EXAMPLE 35

9-Hydroxy-2-(2-hydroxyethyl)pyrazolo[1,5-c]quinazolin-5(6H)-one

Method A 29.2 g (0.1 mole) of 9-(benzyloxy)-2-(2-hydroxyethyl)pyrazolo[1,5-c]quinazolin-5(6H)-one and 0.5 g 10% palladiumon-carbon in 200 ml ethanol containing 0.2 moles of hydrogen chloride are hydrogenated on a Parr shaker, with cooling, at ambient temperature. The reaction is stopped after 0.3 moles of hydrogen are absorbed or when hydrogen uptake ceases, whichever comes first. The reaction is diluted with chloroform, filtered and the filtrate evaporated. The residue is suspended in methylene chloride and shaken with excess aqueous sodium bicarbonate. The organic phase is washed with water, dried and evaporated to give the title compound.

Method B

Following the procedure of Example 35, Method A, but substituting Raney nickel and methanol for the 10% palladiumon-carbon and ethanol, respectively, in Example 35, Method A, and running the reaction at an initial hydrogen pressure of 7 atm., gives the title compound.

EXAMPLE 36

2-(Hydroxyethyl)-9-methoxy-6-methyl-pyrazolo[1,5-c]quinazolin-5(6H)-one

Following the procedure of Example 12, but substituting 9-hydroxy-2-(hydroxyethyl)pyrazolo[1,5-c]quinazolin-5(6H)-one for 2-(hydroxymethyl)-pyrazolo[1,5-c]-quinazolin-5(6H)-one in Example 13 and using twice the amount of the other reagents and solvents employed in Example 12, the title compound is obtained.

EXAMPLE 37

2-(Hydroxymethyl)pyrazolo[1,5-c]quinazolin-5(6H)-one

Following the procedure of Example 25, but substituting 2-[(acetoxy)methyl]pyrazolo[1,5-c]quinazoline-5(6H)-one for 1-methylpyrazolo[1,5-c]quinazoline-5(6H)-one-2-carboxylic acid ether ester in Example 25 and using a mole ratio of 2 to 1 for the quantity of potassium hydroxide to ester, the title compound is obtained.

EXAMPLE 38

5,6-Dihydro-5-oxopyrazolo[1,5-c]quinazoline-2-carboxaldehyde

Method A 2.2 g of 2-(hydroxymethyl)pyrazolo[1,5-c]quinazolin-5(6H)-one (0.01 mole) and 10 g of activated manganese dioxide are stirred in 750 ml $CHCl_3$ at 40°–50° for 60 hours. The reaction mixture is diluted with 300 ml $CH_3OH$, stirred for ~10 minutes and filtered through a Celite pad. The Celite pad is washed with ca. 600 ml of a mixture of $CH_3OH:CHCl_3$ (1:1) and the clear filtrates are combined and stripped to dryness to give 1.5 g of title compound. This material is dissolved in 700 ml absolute ethanol, filtered while hot and the clear filtrate concentrated to ~200 ml. The concentrate is cooled and filtered to give the purified title compound.

Method B

Sodium dichromate dihydrate (29.8 g) in 80 ml of glacial acetic acid at 40° is added during a five minute period to 21.4 g of 2-(hydroxymethyl)pyrazolo[1,5-c]quinazolin-5(6H)-one in 300 ml glacial acetic acid at 60°. Thirty minutes later 1,400 ml of water is added, the mixture is heated to 80° C, cooled, filtered and the residue dried to give the title compound.

EXAMPLE 39

2-[(Acetyloxy)methyl]pyrazolo[1,5-c]quinazolin-5(6H)-one 2.0 g of diazooxindole (0.013 mole) and 12.8 g (0.13 mole or 10 equivalents) of propargyl acetate are refluxed under argon for 4 hours. The reaction mixture is cooled, diluted with 200 ml of ether, stirred for 30 minutes and filtered. The light tan product is washed with ether, dried in vacuo for 1 hour at room temperature and treated with activated charcoal in a mixture of ethanol (200 ml) and ethyl acetate (100 ml). The reaction mixture is filtered through a Celite pad, concentrated to a volume ~100 ml, diluted with 100 ml ethyl acetate and concentrated to a volume of 50 ml. Another 100 ml of ethyl acetate is added, the resulting solution is concentrated to a volume of 50 ml and cooled to 0°–5°. The title compound is filtered off and dried.

EXAMPLE 40

2-(Hydroxymethyl)-7-(trifluoromethyl)pyrazolo[1,5-c]quinazolin-5(6H)-one

A. 7-(Trifluoromethyl)isatin-3-tosylhydrazone 10.0 g (0.0465 mole) of 7-(trifluoromethyl)isatin and 9.4 g (1.05 equivalents) of 97% p-toluenesulfonyl hydrazide are stirred with slight heating in methanol (250 ml) for 15 minutes and then overnight at room temperature. The reaction mixture is concentrated to ½ its original volume and the yellow precipitates that form are filtered off, washed with a small amount of methanol and dried in vacuo at room temperature for 3 hours. Yield: 13.4 g; 75.8% crude yield.

The crude product is taken up in methanol (450 ml) and the clear solution is concentrated to a volume of 100 ml. The solution is cooled and the yellow product is filtered off, washed with a small volume of methanol and dried in vacuo at room temperature for 48 hours and at 75° for 24 hours to give 11.6 g of the tosylhydrazone derivative.

B. 7-(Trifluoromethyl)-3-diazooxindole 11.5 g (0.03 mole) of the 7-(trifluoromethyl)isatin tosylhydrazone is suspended in 345 ml of 0.2 N NaOH and stirred with slight heating for 1 hour and overnight at room temperature. The reaction mixture is saturated with $CO_2$ (dry ice used), stirred for 30 minutes and the precipitates that form are filtered off, washed with a small amount of water and then dried in vacuo for 3 hours at 75°. The crude product is taken up in methanol (200 ml), concentrated down to a volume of 20 ml. Yield: 3.68 g, mp 173°–175°; light orange needles. The product is dried in vacuo at 50° for 2 hours.

C. 2-(Hydroxymethyl)-7-(trifluoromethyl)pyrazolo-[1,5-c]quinazolin-5(6H)-one 2.0 g (0.0088 mole) of 7-(trifluoromethyl)-3-diazooxindole and 10.2 g (0.176 mole or 20 equivalents) of 97% propargyl alcohol are refluxed under $N_2$ for 4 hours, cooled, diluted with ether (200 ml) and stirred for 30 minutes. The light pink solid that forms is filtered off. Yield: 1.3 g; 52.2% crude yield.

The product is taken up in absolute ethanol (150 ml), treated with activated carbon, filtered through a Celite pad and the pad washed with hot absolute ethanol (25 ml). The combined filtrates are concentrated to a volume of ~10 ml, cooled, and the title compound is filtered off and dried, mp 230°–232°.

EXAMPLE 41

10-Chloro-2-(hydroxymethyl)pyrazolo[1,5-c]quinazolin-5(6H)-one

A. 4-Chloroisatin-3-tosylhydrazone 10.0 g (0.055 mole) of 4-chloroisatin and 11.1 g (1.05 equivalents) of 97% p-toluenesulfonyl hydrazide are stirred together in methanol (235 ml) with slight heating for 15 minutes and at room temperature for ~21 hours. The reaction mixture is concentrated to ½ its original volume and the bright yellow precipitates that form are filtered off and dried in vacuo at room temperature for 3 hours. Yield: 18.15 g, mp 195°–196°; 94% yield (crude). The crude product is taken up in dioxane (400 ml) and concentrated down to a volume of 100 ml. The solution is cooled and the yellow product is filtered off, washed with a small amount of methanol and dried in vacuo for 48 hours and at 75° for 24 hours. Yield: 15.15 g, mp 203°–204°.

B. 4-Chloro-3-diazooxindole 15.0 g (0.043 mole) of the 4-chloroisatin tosylhydrazone is taken up in 48 ml of 0.2 N NaOH with slight heating for 1 hour. Methylene chloride (200 ml) is added and stirring continued at room temperature for the next 24 hours. The organic layer is stripped off in a rotary evaporator and the remaining aqueous phase saturated with solid carbon dioxide. The reaction mixture is stirred for 30 minutes and the gold-colored precipitates are filtered off, washed with water and dried in vacuo for 3 hours at 60°–70°. Yield: 8.2 g, mp 214°–215°; 98.6% crude yield.

The crude product is taken up in methanol (600 ml), the light reddish-brown solution is concentrated to a volume of 200 ml, cooled and the burnt-orange product filtered off and dried overnight in vacuo at 60°–70°; yield: 7.5 g, mp 216°–217°.

C.
10-Chloro-2-(hyroxymethyl)pyrazolo[1,5-c]quinazolin-5(6H)-one 2.0 g (0.0103 mole) of 4-chloro-3-diazooxindole, and 11.95 g (0.207 mole or 20 equivalents) of 97% propargyl alcohol are refluxed under $N_2$ for hours. The reaction mixture is cooled, diluted with ether (200 ml) and stirred for 20 minutes. The cream-colored precipitates are filtered off, washed with ether and dried in vacuo over the weekend at 50°. Yield: 2.44 g, mp 295°–296°; 94.9% crude yield. The crude product is taken up in absolute ethanol, filtered while hot and the filtrate is concentrated to a volume of 150 ml. The solution is cooled and the precipitates filtered off, washed with ether and dried in vacuo at room temperature for 24 hours to give 1.4 g of title compound, mp 309°–311°.

EXAMPLE 42

2-(Hydroxymethyl)-10-methoxy-pyrazolo[1,5-c]quinazolin-5(6H)-one

A. 5-(6-Methoxy-2-nitrophenyl)-3-methylpyrazole

Method 1. 5.3 g of (6-methoxy-2-nitrobenzoyl)acetone and a 30-fold excess of hydrazine in a minimum amount of ethanol are heated on a steam bath for 20 minutes. The reaction is cooled and the product is filtered off and dried.

Method 2. 1.9 g of 3-acetyl-4-methoxyindole, 4 g of hydrazine hydrate and 0.15 g hydrazine hydrochloride in 5 ml of ethylene glycol are heated for 3 hours at 160° C. The reaction mixture is cooled, dilute hydrochloric acid is added, filtered, and the filtrate made alkaline with ammonium hydroxide. The alkaline solution is extracted with ether, the ether is washed with water, dried and evaporated to give the crude title compound which can be further purified by recrystallization of its picrate salt followed by liberation of the free base.

B. (2-Amino-6-methoxyphenyl)-3-methylpyrazole

Method 1. 23 g of (6-methoxy-2-nitrophenyl)-3-methylpyrazole and 0.5 g 10% palladium-on-carbon in 200 ml ethanol containing 0.2 moles of hydrogen chloride are hydrogenated on a Parr shaker, with cooling, at ambient temperature. The reaction is stopped after 0.3 moles of hydrogen are absorbed or when hydrogen uptake ceases, whichever comes first. The reaction is diluted with chloroform, filtered and the filtrate evaporated. The residue is suspended in methylene chloride and shaken with excess aqueous sodium bicarbonate. The organic phase is washed with water, dried and evaporated to give the title compound.

Method 2. Following the procedure of Example 42, part B, Method 1, but substituting Raney nickel and methanol for the 10% palladium-on-carbon and ethanol, respectively, in Example 42, part B, Method 1, and running the reaction at an initial hydrogen pressure of 7 atm., gives the title compound.

C.
10-Methoxy-2-methyl-pyrazolo[1,5-c]quinazolin-5(6H)-one

Method 1. Pyridine, 16 g (0.2 mole) and 109 g (0.11 mole) of a solution of 12.5% phosgene in benzene are added to a stirred suspension of 20.3 g (0.1 mole) of 3-methyl-5-(2-amino-6-methoxyphenyl)pyrazole in 100 ml of methylene chloride. After stirring overnight, the product is collected, washed with water and methanol and dried.

Method 2. To 10.1 g (0.05 mole) of 3-methyl-5-(2-amino-6-methoxyphenyl)pyrazole in 100 ml of ethylene dichloride is added 100 ml of water. The resulting mixture is stirred thoroughly while phosgene is slowly introduced. The mixture is maintained basic by the periodic addition of 10% sodium hydroxide solution. During the course of the reaction, a light colored precipitate forms. After about 1 hour, the aqueous layer remains basic. The mixture is flushed thoroughly with nitrogen to remove excess phosgene, and the product is collected and dried.

D.
10-Methoxy-5,6-dihydro-5-oxopyrazolo[1,5-c]quinazoline-2-carboxaldehyde Following the procedure of Example 28, but substituting 10-methoxy-2-methyl-pyrazolo[1,5-c]quinazolin-5(6H)-one for 1-methyl-pyrazolo[1,5-c]quinazolin-5(6H)-one in Example 28, the title compound is obtained.

E.
2-(Hydroxymethyl)-10-methoxy-pyrazolo[1,5-c]-quinazolin-5(6H)-one

Following the procedure of Example 5, part B, but substituting 10-methoxy-5,6-dihydro-5-oxopyrazolo[1,5-c]-quinazoline-2-carboxaldehyde for 2-acetyl-1-methyl-pyrazolo-[1,5-c]quinazolin-5 (6H)-one in Example 5, part B, the title compound is obtained.

EXAMPLE 43

2-[(Acetoxy)methyl]pyrazolo[1,5-c]quinazolin-5(6H)-one

A. 3-(Acetoxymethyl)-5-(2-nitrophenyl)pyrazole

Following the procedure of Example 11, part C, but substituting 5-(2-nitrophenyl)pyrazole-3-carboxylic acid for 5,6-dihydro-5-oxopyrazolo[1,5-c]quinazoline-2-acetic acid in Example 11, part C, and thereafter treating the resulting alcohol in the manner set forth in Example 10, the product is obtained.

B. 3-[(Acetoxy)methyl]-5-(2-aminophenyl)pyrazole

Method 1. 6.5 g of 3-(acetoxymethyl)-5-(2-nitrophenyl)pyrazole is added to a stirred suspension of 115 g iron powder, 730 ml ethanol, 300 ml acetic acid and 210 ml water at reflux. After 2 hours, the reaction is filtered, the filtrate evaporated and the residue treated with dilute aqueous ammonium hydroxide. Extraction with methylene chloride followed by washing of the extracts with water, drying and evaporation of the solvent affords the product.

Method 2. 2.74 g of 3-(acetoxymethyl)-5-(2-nitrophenyl)-pyrazole and 10.5 g stannous chloride in 40 ml concentrated hydrochloric are heated on a steam bath for 1 hour, and then evaporated. The residue is dissolved in water, saturated with hydrogen sulfide until the tin no longer precipitates and filtered. The filtrate is treated with ammonium hydroxide until no further precipitate forms and the product is filtered off and dried.

Method 3. 11.7 g of 3-(acetoxymethyl)-5-(2-nitrophenyl)-pyrazole and 1.2 g of Raney nickel in 200 ml dry methanol is hydrogenated at 40.8 psi hydrogen pressure with shaking until a pressure drop 8.9 psi is observed. The reaction mixture is filtered through Celite; the pad is washed with dry methanol and the filtrate evaporated to give the product.

C.

2-[(Acetoxy)methoxy]pyrazolo[1,5-c]quinazolin-5(6H)-one

Following the procedure of Example 42, part C, but substituting 3-(acetoxymethyl)-5-(2-aminophenyl)-pyrazole for 3-methyl-5-(2-amino-6-methoxyphenyl)-pyrazole in Example 42, part C, the title compound is obtained.

EXAMPLE 44

2-(Hydroxymethyl)-10-methoxypyrazolo[1,5-c]quinazoline-5(6H)-one

To 4.2 g of 10-hydroxy-2-(hydroxymethyl)-pyrazolo[1,5-c]-quinazoline-5(6H)-one in a solution of 0.58 g sodium dissolved in 100 ml dry methanol is added 2.9 g of methyl iodide. After stirring for 3 hours at 50°, the reaction is neutralized with one equivalent of 1N hydrochloric acid, evaporated and the residue recrystallized from absolute ethanol to give the title compound.

EXAMPLES 44a TO 80

Following the procedures of Example 5, but substituting the compounds indicated in Column I of Table I below for 1-methyl-2-diazooxindole and the compounds indicated in Column II below for butyn-2-one in Example 5, the compounds indicated in Column III are obtained.

TABLE I

| | Column I | | | Column II | | | Column III | | | |
|---|---|---|---|---|---|---|---|---|---|---|
| Ex. No. | $R^4$(position) | $R^5$(position) | $R^1$ | $Z_1$ | $R^9$ | | $R^4$ | $R^5$ | $R^1$ | $Z_1$ $R^9$ |
| 44a | s-$C_4H_9$(5) | H | H | —($CH_2$)$_2$— | $C_5H_{11}$ | | s-$C_4H_9$(9) | H | as per column II | |
| 45 | $CH_3$(7) | $CH_3$(6) | $CH_3$ | $CH_2$ | $C_8H_{17}$ | | $CH_3$(7) | $CH_3$(8) | | |
| 46 | n-$C_3H_7$(6) | H | $C_4H_9C(O)CH_2$— | $CH_2$ | $C_4H_9$ | | n-$C_3H_7$(8) | H | | |
| 47 | $CH_3$(5) | $CH_3$(6) | H | $CH_3$-CH— | $CH_3$ | | $CH_3$(9) | H | | |
| 48 | $C_2H_5$(4) | H | H | $C_2H_5$-$CH_2CH$— | —$CH_2$-⌬ | | $C_2H_5$(10) | H | | |
| 49 | $CH_3O$(4) | H | $CH_3C$(O)— | $CH_3$-C-$CH_2$- / $CH_3$ | $C_2H_5$ | | $CH_3O$(10) | H | | |
| 50 | $C_2H_5O$(5) | H | $CH_3$ | $CH_2$ | $CH_3$ | | $C_2H_5O$(9) | H | | |
| 51 | $CH_3O$(4) | H | $C_2H_5C$(O)— | —$CH_2$—($CH_2$)$_2$— | $C_5H_{11}$ | | $CH_3O$(10) | OH | | |
| 52 | $CH_3O$(5) | OH(6) | H | —$CH_2$— / $CH_2$ | $C_2H_5$ | | $CH_3O$(9) | OCH$_3$(7) | | |
| 53 | OH(5) | OCH$_3$(7) | H | —($CH_2$)$_2$— | $C_2H_5$ | | OH(9) | H | | |
| 54 | OH(5) | H | $C_2H_5$ | —($CH_2$)$_3$— | $CH_3$ | | OH(9) | H | | |
| 55 | $CH_3O$(5) | H | $CH_3C$(O)— $CH_3$ | —$CH_2$— | $C_2H_5$ | | $CH_3O$(9) | H | | |
| 56 | ⌬—$CH_2$—O—(5) | H | $C_2H_5C$(O)— $CH_3$ | $CH_3$-C-$CH_3$ / —$CH_2$— / —$CH_2$— | $C_4H_{13}$ —$CH_2$-⌬—OCH$_3$ | | $CH_2O$(9) | H | | |
| 57 | Br(5) | H | H | —($CH_2$)$_2$— | $CH_2$-⌬ | | Br(9) | H | | |
| 58 | Cl(4) | $CH_3$(7) | H | —$CH_2$— | $C_4H_9$ | | Cl(10) | $CH_3$(7) | | |
| 59 | Cl(6) | H | H | $C_2H_5$ / —$CH_2$—$CH$— | $CH_3$ | | Cl(8) | H | | |
| 60 | $CF_3$(7) | H | $CH_3$ | —$CH_2$— | ⌬ | | $CF_3$(7) | H | | |
| 61 | $CF_3$(5) | $CF_3$(6) | $CH_3$ | —$CH_3$-$CH$— | | | $CF_3$(9) | $CF_3$(8) | | |

EXAMPLES 81 TO 118

Following the procedure of Example 22 or 23, but substituting the compounds indicated in Column I of Table II below for 3-diazooxindole and the compounds indicated in Column II below for propargyl alcohol in Example 22 or 23, the compounds indicated in Column III are obtained.

TABLE II

| | Column I | | | | Column II $R^1-C\equiv C-R^2$ | | Column III | | |
|---|---|---|---|---|---|---|---|---|---|
| Ex. No. | $R^4$ | $R^3$ | | $R^5$ | $R^1$ | $R^2$ | $R^4$ | $R^5$ | $R^1 R^2 R^3$ |
| | | | | | | | | | as per column I, as per column II |
| 82 | H | $CH_3$ | | H | H | $CH_2OH$ | H | H | |
| 83 | H | $C_2H_5$ | | H | H | $CH_2CH_2OH$ | H | H | |
| 84 | H | $i-C_3H_7$ | | H | $CH_3$ | $CHOH-CH_3$ | H | H | |
| 85 | H | $CH_2$-(4-Cl-C$_6$H$_4$) | | H | H | $CH_2OH$ | H | H | |
| 86 | H | (2-OCH$_3$-C$_6$H$_4$) | | H | H | $-(CH_2)_3OH$ | H | H | |
| 87 | $CH_3O(7)$ | $CH_3$ | | H | H | $CH_2OH$ | $CH_3O(7)$ | H | |
| 88 | $CH_3O(6)$ | $n-C_4H_9$ | | H | H | $-CHOH-C_6H_5$ | $CH_3O(8)$ | H | |
| 89 | $CH_3O(6)$ | $CH_3$ | | H | H | $CH_2OH$ | $CH_3O(8)$ | H | |
| 90 | $CH_3O(5)$ | $CH_3$ | | H | H | $CH_2OH$ | $CH_3O(9)$ | H | |
| 91 | $CH_3O(4)$ | $CH_3$ | | H | H | $CH_2OH$ | $CH_3O(10)$ | H | |
| 92 | $CH_3O(4)$ | $s-C_4H_9$ | | H | H | $-C(CH_3)(C_6H_5)-OH$ | $CH_3O(10)$ | H | |
| 93 | $CH_3O(4)$ | $CH_2-C_6H_5$ | | H | H | $(CH_2)_4OH$ | $CH_3O(10)$ | H | |
| 94 | $CH_3O(5)$ | $CH_2$-(4-Cl-C$_6$H$_4$) | | H | $CH_3$ | $-CH_2OH$ | $CH_3O(9)$ | H | |
| 95 | $i-C_4H_9(6)$ | $n-C_3H_7$ | | H | $C_2H_5$ | $-C(C_4H_9)(CH_3)-OH$ | $i-C_4H_9(8)$ | H | |
| 96 | $CH_3(4)$ | $CH_3$ | | H | H | $CH_2OH$ | $CH_3(10)$ | H | |

TABLE II-continued

| Ex. No. | Column I (R⁴, R³, R⁵) | | | Column II (R¹, R², R⁴) | | | Column III (R⁵) |
|---|---|---|---|---|---|---|---|
| | R⁴ | R³ | R⁵ | R¹ | R² | R⁴ | R⁵ |
| 97 | CH₃(4) | 3-CF₃-benzyl | H | H | —CH₂OH | CH₃(10) | H |
| 98 | F(5) | CH₃ | H | H | —CH₂OH | F(9) | H |
| 99 | Cl(4) | 4-Cl-CH₂C₆H₄ | CH₃O(7) | CH₃ | —(CH₂)₂OH | Cl(10) | CH₃O(7) |
| 100 | CF₃(7) | C₂H₅ | H | H | —CHOH–CH₂–cyclohexyl | CF₃(7) | H |
| 101 | CH₃CO(5) (C=O) | CH₃ | H | H | —CHOH–C₂H₅ | CH₃CO(9) (C=O) | H |
| 102 | C₆H₅CH₂O(6) | i-C₃H₇ | H | CH₃ | —COH(CH₂)₂OH (cyclopentyl) | C₆H₅CH₂O(8) | H |
| 103 | C₂H₅(5) | 4-OCH₃-benzyl | C₂H₅(6) | HOCH₂ / HOC(CH₃) | i-C₃H₇ / n-C₄H₉ | C₂H₅(9) | C₂H₅(8) |
| 104 | H | CH₃ | H | HOCH₂ | | H | H |
| 105 | H | i-C₃H₇ | H | | | H | H |
| 106 | H | CH₂-C₆H₅ | H | HO(CH₂)₂ | C₆H₅ | H | H |
| 107 | H | 4-Cl-CH₂C₆H₄ | H | | 4-Br-C₆H₄ | H | H |

TABLE II-continued

| | Column I | | | | Column II | | Column III | | |
|---|---|---|---|---|---|---|---|---|---|
| | | | | | $R^1-C\equiv C-R^2$ | | | | |
| Ex. No. | $R^4$ | $R^5$ | $R^3$ | | $R^1$ | $R^2$ | $R^4$ | $R^5$ | |
| 108 | H | H | $CH_2$-(3-$CF_3$-C$_6$H$_4$) | | $HO(CH_2)_4$ | 4-$OCH_3$-C$_6$H$_4$ | H | H | |
| 109 | $CH_3$(5) | H | $CH_3$ | | HOCH$_2$—n-C$_3$H$_7$ | 4-i-C$_4$H$_9$-C$_6$H$_4$ | $CH_3$(9) | H | |
| 110 | n-C$_3$H$_7$(5) | n-C$_3$H$_7$(6) | $C_2H_5$ | | HOCH$_2$ | 4-CH$_3$-C$_6$H$_4$ | n-C$_3$H$_7$(9) | n-C$_3$H$_7$(8) | |
| 111 | $CH_3O(4)$ | H | $CH_3$ | | HOCH$_2$ | n-C$_3$H$_7$ | $CH_3O(10)$ | H | |
| 112 | $CH_3O(4)$ | H | $CH_3$ | | HOCH$_2$ | n-C$_4$H$_9$ | $CH_3O(10)$ | H | |
| 113 | $CH_3O(4)$ | H | $CH_3$ | | HOCH$_2$ | C$_6$H$_5$ | $CH_3O(10)$ | H | |
| 114 | s-C$_4$H$_9$(5) | H | $CH_2$-C$_6$H$_5$ | | $HO(CH_2)_2$ | 3-CF$_3$-C$_6$H$_4$ | s-C$_4$H$_9$(9) | H | |
| 115 | $CH_3CO(6)$ | H | C$_6$H$_5$ | | HOCH— C$_6$H$_5$ | 2-CH$_3$-C$_6$H$_4$ | $CH_3CO(8)$ | H | |
| 116 | Cl(4) | $CH_3$(7) | i-C$_4$H$_9$ | | $HO(CH_2)_3$ | 4-i-C$_3$H$_7$-C$_6$H$_4$ | Cl(10) | $CH_3$(7) | |
| 117 | F(6) | H | C$_2$H$_5$ | | HOCH$_2$CHCH$_2$CH$_3$ | 4-s-C$_4$H$_9$-C$_6$H$_4$ | F(8) | H | |
| 118 | CF$_3$(7) | H | $CH_2$-(4-OCH$_3$-C$_6$H$_4$) | | HOCH$_2$ | 4-OC$_2$H$_5$-C$_6$H$_4$ | CF$_3$(7) | H | |

EXAMPLES 119 TO 154

Following the procedure of Example 2, but substituting the compounds indicated in Column I of Table III below for 3-diazooxindole in Example 2A and the compound indicated in Column II below for ethyl propiolate and thereafter treating the product ester in the manner set out in Example 7 but substituting the compounds indicated in column III for methyl magnesium chloride in Example 7, the compounds indicated in Column IV are obtained.

TABLE III

| | Column I | | | Column II | | Column III | Column IV | | | | |
|---|---|---|---|---|---|---|---|---|---|---|---|
| | ![diazo structure with $R^3$, $R^4$, $R^5$] | | | $R_1'$—C≡C—$R_1''$ | | | ![product structure] | | | | |
| Ex. No. | $R^4$ (position) | $R^5$ (position) | $R^3$ | $R_1'$ | $R_1''$ | RMX | $R^4$ (position) | $R^5$ (position) | $R^3$ | $R^1$ | $R^2$ |
| 119 | H | H | H | H | $CH_2CO_2CH_3$ | $CH_3MgCl$ | H | H | as in column I | H | $-CH_2-C(CH_3)_2-OH$ |
| 120 | H | H | H | H | $CH_2CH_2CO_2CH_3$ | $CH_3MgCl$ | H | H | | H | $-(CH_2)_2-C(CH_3)_2-OH$ |
| 121 | H | H | H | $CO_2CH_3$ | $CO_2CH_3$ | $CH_3MgCl$ | H | H | | $-C(CH_3)_2-OH$ | $-C(CH_3)_2-OH$ |
| 122 | H | H | H | H | $CO_2C_2H_5$ | $C_2H_5MgCl$ | H | H | | H | $-C(C_2H_5)_2-OH$ |
| 123 | H | H | H | H | $CO_2CH_3$ | $CH_3MgCl$ | H | H | | H | $-C(CH_3)_2-OH$ |
| 124 | $CH_3O(7)$ | H | $CH_3$ | 4-$CH_3O$-$C_6H_4$- | H | $CO_2C_2H_5$ | $n$-$C_3H_7MgBr$ | $CH_3O(7)$ | H | H | $-C(n$-$C_3H_7)_2-OH$ |
| 125 | $CH_3O(6)$ | H | H | H | $CO_2CH_3$ | $n$-$C_4H_9MgBr$ | $CH_3O(8)$ | H | | H | $-C(n$-$C_4H_9)_2-OH$ |
| 126 | $CH_3O(6)$ | H | $CH_3$ | H | $CH_2CO_2CH_3$ | $CH_3MgCl$ | $CH_3O(8)$ | H | | H | $-CH_2-C(CH_3)_2-OH$ |

TABLE III-continued

Column I: diazo-indolinone structure with R³ (on N), R⁴, R⁵ (positions on benzene ring), and =N₂, =O
Column II: $R_1^1—C \equiv C—R_1^2$
Column III: RMX
Column IV: product structure with R¹, R², R³, R⁴, R⁵

| Ex. No. | R⁴ (position) | R⁵ (position) | R³ | R₁¹ | R₁² | RMX | R⁴ (position) | R⁵ (position) | R³ | R¹ | R² |
|---|---|---|---|---|---|---|---|---|---|---|---|
| 127 | CH₃O(5) | H | H | H | CO₂C₂H₅ | C₂H₅MgBr | CH₃O(9) | H | H | H | C₂H₅ —COH C₂H₅ |
| 128 | CH₃O(4) | H | H | H | CO₂CH₃ | CH₃MgBr | CH₃O(10) | H | H | H | CH₃ —COH CH₃ |
| 129 | CH₃O(4) | H | s-C₄H₉ | CH₃O₂C | CO₂CH₃ | CH₃MgBr | CH₃O(10) | H | H | H | CH₃ —COH CH₃ |
| 130 | i-C₃H₇O(4) | H | H | H | —CH₂CO₂CH₃ | CH₃MgBr | i-C₃H₇O(10) | H | H | H | CH₃ CH₂COH CH₃ |
| 131 | CH₃O(4) | H | H | H | CO₂CH₃ | C₂H₅MgBr | CH₃O(10) | H | HOC—CH₃ / CH₃ | H | C₂H₅ —COH C₂H₅ |
| 132 | CH₃O(5) | H | —CH₂—C₆H₅ | CH₃ | CO₂CH₃ | i-C₃H₇MgBr | CH₃O(9) | H | H | H | i-C₃H₇ —COH i-C₃H₇ |
| 133 | i-C₄H₉(6) | H | n-C₃H₇ | CH₃ | CO₂C₂H₅ | CH₃MgCl | i-C₄H₉(8) | H | H | CH₃ | CH₃ —COH CH₃ |
| 134 | Cl(4) | H | H | H | CO₂C₂H₅ | CH₃MgCl | Cl(10) | H | H | H | CH₃ —COH CH₃ |

TABLE III-continued

| | Column I | | Column II | | Column III | Column IV | | | |
|---|---|---|---|---|---|---|---|---|---|
| |  | | $R^1_1-C\equiv C-R^2_1$ | | | | | | |
| Ex. No. | $R^4$ (position) | $R^3$ | $R^1_1$ | $R^2_1$ | RMX | $R^4$ (position) | $R^5$ (position) | $R^1$, $R^3$ | $R^2$ |
| 135 | $CH_3(5)$ | H | H | $CO_2CH_3$ | $CH_3MgCl$ | $CH_3(9)$ | H | $CH_3$, H | $CH_3-COH-CH_3$ |
| 136 | Cl(4) | H | $CH_3$ | $(CH_2)_2CO_2CH_3$ | $C_2H_5MgBr$, $CO_2CH_3$ | Cl(10) | $CH_3O(7)$ | $CH_3$, H | $-(CH_2)_2-COH-C_2H_5$ |
| 137 | PhCH_2O(6) | H | $CH_3O_2CCH_2-$ | $CH_2CO_2CH_3$ | $CH_3MgCl$ | PhCH_2O(8) | H | $HOCH_2CH_3$, H | $CH_2-COH-C_2H_5$ |
| 138 | $C_2H_5(5)$ | H | H | $CO_2CH_3$ | $CH_3MgBr$ | $C_2H_5(9)$ | $C_2H_5(8)$ | H, H | $CH_3-COH-CH_3$ |
| 139 | H | H | H | $CO_2C_2H_5$ | Br-Ph-MgBr | H | H | H, H | Br-Ph-C(OH)-Ph-Br |
| 140 | H | H | $CH_3O_2C$ | $i-C_3H_7$ | $CH_3MgBr$ | H | H | $CH_3-COH-CH_3$, H | $i-C_3H_7$ |
| 141 | H | $CH_3$ | $C_2H_5O_2C$ | $n-C_4H_9$ | $CH_3MgBr$ | H | H | $CH_3-COH-CH_3$, $CH_3$ | $n-C_4H_9$ |

TABLE III-continued

| | Column I | | | Column II | | Column III | Column IV | | | |
|---|---|---|---|---|---|---|---|---|---|---|
| | | | | $R_1^1-C\equiv C-R_1^2$ | | | | | | |
| Ex. No. | $R^4$ (position) | $R^5$ (position) | $R^3$ | $R_1^1$ | $R_1^2$ | RMX | $R^4$ (position) | $R^5$ (position) | $R^1$ | $R^2$ |
| 142 | H | H | H | $CH_3O_2C$ | phenyl | $CH_3MgBr$ | H | H | $HOC(CH_3)_2$ | phenyl |
| 143 | H | H | $CH_3$ | $CH_3O_2C(CH_2)_2$ | 4-Br-phenyl | $CH_3MgBr$ | H | H | $HOC(CH_3)(CH_2)_2$— $CH_3$ | 4-Br-phenyl |
| 144 | H | H | —$CH_2$-phenyl | $CH_3O_2C$ | 4-$OCH_3$-phenyl | $CH_3MgBr$ | H | H | $HOC(CH_3)_2$ | 4-$OCH_3$-phenyl |
| 145 | $CH_3(5)$ | H | H | $C_2H_5O_2C-CH_2$— | $i-C_4H_9$ | phenyl-MgBr | $CH_3(9)$ | H | (phenyl)$_2$HOCCH$_2$ | $i-C_4H_9$ |
| 146 | $n-C_3H_7(5)$ | $n-C_3H_7(6)$ | H | $C_2H_5O_2C$ | 4-$CH_3$-phenyl | $CH_3MgBr$ | $n-C_3H_7(9)$ | $n-C_3H_7(8)$ | $HOC(CH_3)_2$-$CH_3$ | 4-$CH_3$-phenyl |
| 147 | $CH_3O(4)$ | H | $CH_3$ | $CH_3O_2C$ | $n-C_3H_7$ | $CH_3MgBr$ | $CH_3O(10)$ | H | $HOC(CH_3)_2$ | $n-C_3H_7$ |
| 148 | $CH_3O(4)$ | H | H | $CH_3O_2C$— | $n-C_4H_9$ | phenyl-MgBr | $CH_3O(10)$ | H | (phenyl)$_2$HOC | as per column II |

TABLE III-continued

| | Column I | | | Column II | Column III | | | Column IV | | |
|---|---|---|---|---|---|---|---|---|---|---|
| Ex. No. | $R^4$ (position) | $R^5$ (position) | $R^3$ | $R^1_1$ | $R^1_2$ | RMX | $R^4$ (position) | $R^5$ (position) | $R^1$ | $R^2$ |
| 149 | $CH_3O(4)$ | H | H | $CH_3\underset{\underset{O}{\parallel}}{C}-$ | cyclohexyl | $CH_3MgBr$ | $CH_3O(10)$ | H | $CH_3\underset{\underset{HO}{\mid}}{C}-CH_3$ | |
| 150 | $s\text{-}C_4H_9(5)$ | H | H | $HC\underset{\underset{O}{\parallel}}{-}$ | 3-$CF_3$-phenyl | $CH_3MgBr$ | $s\text{-}C_4H_9(9)$ | H | $HOCH\text{-}CH_3$ | |
| 151 | $CH_3O(6)$ | H | $CH_3$ | phenyl-C(=O)- | 2-$CH_3$-phenyl | $CH_3MgBr$ | $CH_3O(8)$ | H | $CH_3\underset{\underset{HO}{\mid}}{C}-$(4-$C_2H_5$-phenyl) | |
| 152 | Cl(4) | $CH_3(7)$ | H | $CH_3CH_2\underset{\underset{O}{\parallel}}{C}-$ | $s\text{-}C_4H_9$ | phenyl-MgBr | Cl(10) | $CH_3(7)$ | $CH_3\underset{\underset{HO}{\mid}}{C}-$phenyl | $s\text{-}C_4H_9$ |
| 153 | H | H | $CH_3$ | H | $-CH=O$ | $CH_3MgBr$ | H | H | H | $-\underset{\underset{CH_3}{\mid}}{CHOH}$ |
| 154 | $CH_3O(4)$ | H | H | H | $-CH=O$ | phenyl-MgBr | $CH_3O(10)$ | H | H | $-CHOH$-phenyl |

EXAMPLES 155 TO 183

Following the procedures of Example 11, but substituting the compounds indicated in Column I, Table IV, below for 2-acetylpyrazolo[1,5-c]quinazolin-5(6H)-one in part A of Example 11, the compounds indicated in Column II are obtained.

TABLE IV

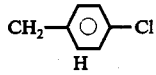

| Ex. No. | R⁴ (position) | R⁵ | R³ | R¹ | R² | R⁴ | R⁵ | R³ | R¹ | R² |
|---|---|---|---|---|---|---|---|---|---|---|
| 155 | H | H | $CH_3$ | H | $-\overset{O}{\overset{\|}{C}}CH_3$ | as per Column I except for R¹ in Ex. 159 | | | | $(CH_2)_2OH$ |
| 156 | H | H | H | H | $-\overset{O}{\overset{\|}{C}}CH_2CH_3$ | | | | | $(CH_2)_3OH$ |
| 157 | H | H | H | H | $-\underset{CH_3}{\overset{\|}{C}HOH}$ | | | | | $(CH_2)_2OH$ |
| 158 | H | H | $CH_2\text{-}C_6H_4\text{-}Cl$ | $CH_3$ | $-\overset{O}{\overset{\|}{C}}CH_3$ | | | | | $(CH_2)_2OH$ |
| 159 | H | H | H | $CH_3\overset{O}{\overset{\|}{C}}-$ | $-\overset{O}{\overset{\|}{C}}CH_3$ | | | | $(CH_2)_2OH$ | $(CH_2)_2OH$ |
| 160 | $CH_3O(7)$ | H | H | H | $-\overset{O}{\overset{\|}{C}}CH_3$ | | | | | $(CH_2)_2OH$ |
| 161 | $CH_3O(8)$ | H | $n\text{-}C_4H_9$ | H | $-\underset{CH_3}{\overset{\|}{C}HOH}$ | as per Column I | | | | $(CH_2)_2OH$ |
| 162 | $CH_3O(8)$ | H | H | H | $-\overset{O}{\overset{\|}{C}}(CH_2)_2CH_3$ | | | | | $(CH_2)_4OH$ |
| 163 | $CH_3O(9)$ | H | $CH_3$ | H | $-\overset{O}{\overset{\|}{C}}CH_2CH_3$ | | | | | $(CH_2)_3OH$ |
| 164 | $CH_3O(10)$ | H | H | H | $-\overset{O}{\overset{\|}{C}}CH_3$ | | | | | $(CH_2)_2OH$ |
| 165 | $CH_3O(10)$ | H | H | H | $-\underset{C_6H_5}{\overset{CH_3}{\overset{\|}{C}}}-OH$ | | | | | $-\underset{C_6H_5}{\overset{\|}{C}HCH_2OH}$ |
| 166 | $CH_3O(10)$ | H | $CH_2\text{-}C_6H_5$ | H | $-\overset{O}{\overset{\|}{C}}CH_3$ | | | | | $-(CH_2)_2OH$ |
| 167 | $CH_3O(9)$ | H | $CH_2\text{-}C_6H_4\text{-}Cl$ | $CH_3$ | $-\overset{O}{\overset{\|}{C}}CH_3$ | | | | | $-(CH_2)_2OH$ |
| 168 | $i\text{-}C_4H_9(8)$ | H | H | $C_2H_5$ | $-\overset{O}{\overset{\|}{C}}CH_3$ | | | | | $-(CH_2)_2OH$ |
| 169 | $CH_3(10)$ | H | H | $-\overset{O}{\overset{\|}{C}}CH_3$ | $-\overset{O}{\overset{\|}{C}}CH_3$ | | | | $-(CH_2)_2OH$ | $(CH_2)OH$ |
| 170 | $CH_3(10)$ | H | $\text{-}C_6H_4\text{-}CF_3$ | H | $-\overset{O}{\overset{\|}{C}}CH_3$ | as per column I except for R¹ in Ex. 169 | | | | $-(CH_2)_2OH$ |
| 171 | F(9) | H | H | H | $-\overset{O}{\overset{\|}{C}}CH_2CH_3$ | | | | | $-(CH_2)_3OH$ |
| 172 | Cl(10) | $CH_3O(7)$ | H | $CH_3$ | $-\overset{O}{\overset{\|}{C}}CH_2CCH_3$ | | | | | $-(CH_2)_3OH$ |
| 173 | $CF_3(7)$ | H | $C_2H_5$ | H | $-\underset{CH_3}{\overset{\|}{C}HOH}$ | | | | | $-(CH)_2OH$ |

TABLE IV-continued

| | Column I | | | | | Column II | | | |
|---|---|---|---|---|---|---|---|---|---|
| Ex. No. | R⁴ (position) | R⁵ | R³ | R¹ | R² | R⁴ | R⁵ | R³ | R¹ | R² |

| Ex. No. | R⁴ (position) | R⁵ | R³ | R¹ | R² | R⁴ R⁵ R³ R¹ | R² |
|---|---|---|---|---|---|---|---|
| 174 | CH₃O(9) | H | H | H | -C(=O)C₂H₅ | | -(CH₂)₃OH |
| 175 | H | H | H | H | CH₃C(=O)- | i-C₃H₇ | as per Column I | HO(CH₂)₂- | as per Column I |
| 176 | H | H | i-C₃H₇ | C₂H₅\|HOCH- | n-C₄H₉ | | HO(CH₂)₃- |
| 177 | H | H | H | H₃CC(=O)- | phenyl | | HO(CH₂)₂ |
| 178 | H | H | CH₂-⌬-Cl | CH₃(CH₂)₂-C(=O)- | -⌬-Br | | HO(CH₂)₄- |
| 179 | H | H | CH₂-⌬-CF₃ | CH₃-C(=O)- | -⌬-OCH₃ | | HO(CH₂)₂- |
| 180 | CH₃(9) | H | H | HOCH-\|n-C₃H₇ | i-C₄H₉ | | HO(CH₂)₄- |
| 181 | CH₃O(10) | H | H | CH₃C(=O)- | n-C₃H₇ | | HO(CH₂)₂- |
| 182 | CH₃O(10) | H | CH₃ | CH₃CH₂C(=O)- | n-C₄H₉ | | HO(CH₂)₃- |
| 183 | CH₃O(10) | H | H | CH₃C(=O)- | phenyl | | HO(CH₂)₂- |

EXAMPLES 184 TO 205

Following the procedure of Example 43, but substituting the compounds indicated in Column I below for 5-(2-nitrophenyl)-pyrazole-3-carboxylic acid in part A, the compounds indicated in Column II are obtained.

TABLE V

| | Column I | | Column II | |
|---|---|---|---|---|
| Ex. No. | R⁴ (position) | R⁵ (position) | R⁴ (position) | R⁵ |
| 184 | H | H | H | as per column I |
| 185 | H | H | H | |
| 186 | H | H | H | |
| 187 | H | H | H | |
| 188 | H | H | H | |
| 189 | CH₃O(3) | H | CH₃O(7) | |
| 190 | CH₃O(4) | H | CH₃O(8) | |
| 191 | CH₃O(4) | H | CH₃O(8) | |
| 192 | CH₃O(5) | H | CH₃O(9) | |
| 193 | CH₃O(6) | H | CH₃O(10) | |
| 194 | CH₃O(6) | H | CH₃O(10) | |
| 195 | C₃H₇O(6) | H | C₃H₇O(10) | |
| 196 | CH₃O(6) | H | CH₃O(10) | |
| 197 | CH₃O(5) | H | CH₃O(9) | |

TABLE V-continued

Column I: R⁴, R⁵-substituted phenyl with CH=C-N(H)-N=C-CO₂H, NO₂ group

Column II: R⁴, R⁵-substituted phenyl with CH=C-N-N=C-CH₂OCCH₃, with NH-C(=O) ring

| Ex. No. | R⁴ (position) | R⁵ (position) | R⁴ (position) | R⁵ |
|---|---|---|---|---|
| 198 | i-C₄H₉(4) | H | i-C₄H₉(8) | |
| 199 | CH₃(6) | H | CH₃(10) | H |
| 200 | CH₃(5) | H | CH₃(9) | H |
| 201 | F(5) | H | F(9) | H |
| 202 | Cl(6) | CH₃O(3) | Cl(10) | CH₃O(7) |
| 203 | CF₃(3) | H | CF₃(7) | H |
| 204 | C₆H₅—CH₂O(6) | H | C₆H₅—CH₂O(10) | H |
| 205 | CH₃CO(5) (O=) | H | CH₃CO(9) (O=) | H |

EXAMPLES 206 TO 286

Following the procedure of Example 22 or 23 but substituting for 3-diazooxindole, the compound shown in column I of Table VI below, and substituting for propargyl alcohol, the compound shown in column II below, the compound of the invention shown in column III is obtained.

TABLE VI

Column I: R⁴, R⁵-substituted indole with N₂, NH, =O

Column II: Q—Z—C≡C—R²

Column III: R⁵, R⁴-substituted phenyl with pyrazole ring bearing Q—Z, R², and NH-C(=O)

| Ex. No. | R⁴ (position) | R⁵ (position) | Q | Z | R² | R⁴ (position) | R⁵ (position) | Q | Z | R² |
|---|---|---|---|---|---|---|---|---|---|---|
| 206 | CH₃(6) | H | HO— | CH₂ | C₆H₅ | CH₃(8) | H | as per column II | | |
| 207 | CH₃(5) | H | HO— | —(CH₂)₂— | n-C₃H₇ | CH₃(9) | H | | | |
| 208 | i-C₃H₇(5) | H | HO— | —(CH₂)₂— | n-C₄H₉ | i-C₃H₇(9) | H | | | |
| 209 | CH₃(5) | CH₃(6) | HO— | —CH(CH₃)— | t-C₄H₉ | CH₃(9) | CH₃(8) | | | |
| 210 | H | H | HO— | —(CH₂)₃— | n-C₃H₇ | H | H | | | |
| 211 | C₂H₅(4) | H | HO— | —(CH₂)₂— | p-CH₃-C₆H₄ | C₂H₅(10) | H | | | |
| 212 | n-C₃H₇O(6) | H | HO— | —CH₂— | s-C₄H₉ | n-C₃H₇O(8) | H | | | |
| 213 | CH₃CO(5) (O=) | H | HO— | —CH₂— | o-Cl-C₆H₄ | CH₃CO(9) (O=) | H | | | |
| 214 | CH₃CO(5) (O=) | CH₃CO(6) (O=) | HO— | —(CH₂)₃— | n-C₄H₉ | CH₃CO(9) (O=) | CH₃CO(8) (O=) | | | |
| 215 | CH₃O(4) | H | HO— | —CH₂— | m-F-C₆H₄ | CH₃O(10) | H | | | |
| 216 | OH(5) | H | HO— | —CH(CH₃)— | C₆H₅ | OH(9) | H | | | |
| 217 | Br(6) | H | HO— | —CH(C₂H₅)— | i-C₃H₇ | Br(8) | H | | | |
| 218 | Cl(5) | Cl(6) | HO— | CH₂ | m-CF₃-C₆H₄ | Cl(9) | Cl(8) | | | |
| 219 | C₂H₅(5) | C₂H₅(6) | HO— | CH₂ | —n-C₄H₉ | C₂H₅(9) | C₂H₅(8) | | | |
| 220 | CF₃(6) | H | HO— | —CH₂CH(CH₃)CH₂— | p-F-C₆H₄ | CF₃(8) | H | | | |

TABLE VI-continued

| | Column I | | | Column II | | | Column III | |
|---|---|---|---|---|---|---|---|---|
| Ex. No. | $R^4$ (position) | $R^5$ (position) | Q | Z | $R^2$ | $R^4$ (position) | $R^5$ (position) | Q Z $R^2$ |
| 221 | $NO_2(5)$ | H | HO— | $-(CH_2)_2-$ | $i-C_4H_9$ | $NO_2(9)$ | H | |
| 222 | $NO_2(4)$ | H | HO— | $CH_2$ | $OC_3H_7$ phenyl | $NO_2(10)$ | H | |
| 223 | OH(5) | OH(6) | HO— | $CH_2$ | $t-C_4H_9$ | OH(9) | OH(8) | |
| 224 | OH(5) | H | HO— | $-(CH_2)_2-$ | $t-C_4H_9$ | OH(9) | H | |
| 225 | $CH_3O(4)$ | H | HO— | $-CH_2-$ | phenyl | $CH_3O(10)$ | H | |
| 226 | $CH_3O(4)$ | H | HO— | $-CH_2-$ | $n-C_3H_7$ | $CH_3O(10)$ | H | |
| 227 | $CH_3O(4)$ | H | HO— | $-CH_2-$ | phenyl | $CH_3O(10)$ | H | |
| 228 | $CH_3O(4)$ | H | HO— | $-CH_2-$ | $n-C_3H_7$ | $CH_3O(10)$ | H | |
| 229 | $CH_3O(4)$ | H | HO— | $-CH_2-$ | $i-C_3H_7$ | $CH_3O(10)$ | H | |
| 230 | $CH_3O(4)$ | H | HO— | $-CH_2-$ | $n-C_4H_9$ | $CH_3O(10)$ | H | |
| 231 | $CH_3O(4)$ | H | HO— | $-CH_2-$ | $i-C_4H_9$ | $CH_3O(10)$ | H | |
| 232 | $C_2H_5O(4)$ | H | HO— | $-(CH_2)_2-$ | $n-C_3H_7$ | $C_2H_5O(10)$ | H | |
| 233 | $CH_3O(4)$ | H | HO— | $-(CH_2)_3-$ | $n-C_3H_7$ | $CH_3O(10)$ | H | |
| 234 | $CH_3O(5)$ | H | HO— | $-CH_2-$ | phenyl | $CH_3O(9)$ | H | |
| 235 | $CH_3O(5)$ | H | HO— | $-CH_2-$ | $n-C_4H_9$ | $CH_3O(9)$ | H | |
| 236 | $CH_3O(6)$ | H | HO— | $-CH_2-$ | $n-C_3H_7$ | $CH_3O(8)$ | H | |
| 237 | $i-C_3H_7O(6)$ | H | HO— | $-(CH_2)_2-$ | phenyl | $i-C_3H_7O(8)$ | H | |
| 238 | $CH_3O(7)$ | H | HO— | $-CH_2-$ | $n-C_4H_9$ | $CH_3O(7)$ | H | |
| 239 | $CH_3O(7)$ | H | HO— | $-(CH_2)_2-$ | phenyl | $CH_3O(7)$ | H | |
| 240 | $CH_3O(7)$ | Cl(4) | HO— | $-(CH_2)_2-$ | $n-C_3H_7$ | $CH_3O(7)$ | Cl(10) | |
| 241 | $CH_3O(4)$ | H | $n-C_3H_7O$ | $-CH_2-$ | phenyl | $CH_3O(10)$ | H | |
| 242 | $CH_3O(5)$ | H | $s-C_4H_9O$ | $-CHCH_2-$ <br> $\|$ <br> $CH_3$ | $n-C_3H_7$ | $CH_3O(9)$ | H | |
| 243 | $C_2H_5(5)$ | $C_2H_5(6)$ | phenyl-O— | $-CH_2-$ | $i-C_4H_9$ | $C_2H_5(9)$ | $C_2H_5(8)$ | |
| 244 | F(5) | H | phenyl-$CH_2C(O)-$ | $-CH_2-$ | $CH_3$ | F(9) | H | |
| 245 | Cl(4) | H | phenyl-$CH_2O-$ | $-(CH_2)_3-$ | phenyl | Cl(10) | H | |
| 246 | $CF_3(7)$ | H | $CH_3OCH_2-$ | $-CH_2-$ | $CH_2OCH_3$ | $CF_3(7)$ | H | |
| 247 | $CH_3(6)$ | H | $CH_3C(O)O-$ | $-CH_2-$ | phenyl | $CH_3(8)$ | H | |
| 248 | $CH_3(5)$ | H | $CH_3C(O)O-$ | $-(CH_2)_2-$ | $n-C_3H_7$ | $CH_3(9)$ | H | |
| 249 | $i-C_3H_7(5)$ | H | $CH_3C(O)O-$ | $-(CH_2)_2$ | $n-C_4H_9$ | $i-C_3H_7(9)$ | H | |
| 250 | $CH_3(5)$ | $CH_3(6)$ | $C_2H_5-C(O)O-$ | $-CH-$ <br> $\|$ <br> $CH_3$ | $t-C_4H_9$ | $CH_3(9)$ | $CH_3(8)$ | |
| 251 | H | H | $CH_3C(O)O-$ | $-(CH_2)_3-$ | $n-C_3H_7$ | H | H | |
| 252 | $C_2H_5(4)$ | H | $HCOO-$ | $-(CH_2)_2-$ | phenyl-$CH_3$ | $C_2H_5(10)$ | H | |
| 253 | $n-C_3H_7O(6)$ | H | phenyl-$CH_2-C(O)O-$ | $-CH_2-$ | phenyl-Cl | $n-C_3H_7O(8)$ | H | |

TABLE VI-continued

| Column I | | Column II | | | Column III | | | | |
|---|---|---|---|---|---|---|---|---|---|
| Ex. No. | $R^4$ (position) | $R^5$ (position) | Q | Z | $R^2$ | $R^4$ (position) | $R^5$ (position) | Q | Z | $R^2$ |
| 254 | $CH_3CO$(5) | H | 3-Cl-C$_6$H$_4$-CH$_2$-CO- | $-(CH_2)_3-$ | n-C$_4$H$_9$ | $CH_3CO$(9) | H | | | |
| 255 | $CH_3CO$(5) | $CH_3CO$(6) | C$_4$H$_9$CO- | $-CH_2-$ | 4-F-C$_6$H$_4$- | $CH_3CO$(9) | $CH_3CO$(8) | | | |
| 256 | $CH_3O$(4) | H | $CH_3C(=O)$- | $-CH(CH_3)-$ | C$_6$H$_5$- | $CH_3O$(10) | H | | | |
| 257 | OH(5) | H | $CH_3CO$- | thiacyclohexyl | 4-CH$_3$O-C$_6$H$_4$- | OH(9) | H | | | |
| 258 | Br(6) | H | $CH_3CO$- | $-CH(C_2H_5)-$ | i-C$_3$H$_7$ | Br(8) | H | | | |
| 259 | Cl(5) | Cl(6) | $C_2H_5CO$- | $-CH_2-$ | 3-CF$_3$-C$_6$H$_4$- | Cl(9) | Cl(8) | | | |
| 260 | C$_2$H$_5$(5) | C$_2$H$_5$(6) | C$_6$H$_5$-CO- | $-CH_2-$ | n-C$_4$H$_9$ | C$_2$H$_5$(9) | C$_2$H$_5$(8) | | | |
| 261 | CF$_3$(6) | H | $CH_3CO$- | $-CH_2CH(CH_3)CH_2-$ | 4-F-C$_6$H$_4$- | CF$_3$(8) | H | | | |
| 262 | NO$_2$(5) | H | C$_3$H$_7$CO- | $-(CH_2)_2-$ | i-C$_4$H$_9$ | NO$_2$(9) | H | | | |
| 263 | NO$_2$(4) | H | 4-CH$_3$-C$_6$H$_4$-CH$_2$CO- | $-CH_2-$ | 2-OC$_3$H$_7$-C$_6$H$_4$- | NO$_2$(10) | H | | | |
| 264 | OH(5) | OH(6) | i-C$_3$H$_7$CO- | $-CH_2-$ | t-C$_4$H$_9$ | OH(9) | OH(8) | | | |
| 265 | OH(5) | H | 4-CH$_3$O-C$_6$H$_4$-CO- | $-(CH_2)_2$ | t-C$_4$H$_9$ | OH(9) | H | | | |
| 266 | CH$_3$O(4) | H | HCO- | $-CH_2-$ | C$_6$H$_5$- | CH$_3$O(10) | H | | | |
| 267 | CH$_3$O(4) | H | HCO- | $-CH_2-$ | n-C$_3$H$_7$ | CH$_3$O(10) | H | | | |
| 268 | CH$_3$O(4) | H | CH$_3$CO- | $-CH_2-$ | C$_6$H$_5$- | CH$_3$O(10) | H | | | |
| 269 | CH$_3$O(4) | H | CH$_3$CO- | $-CH_2-$ | n-C$_3$H$_7$ | CH$_3$O(10) | H | | | |
| 270 | CH$_3$O(4) | H | CH$_3$CO- | $-CH_2-$ | i-C$_3$H$_7$ | CH$_3$O(10) | H | | | |
| 271 | CH$_3$O(4) | H | CH$_3$CO- | $-CH_2-$ | n-C$_4$H$_9$ | CH$_3$O(10) | H | | | |
| 272 | CH$_3$O(4) | H | CH$_3$CO- | $-CH_2-$ | s-C$_4$H$_9$ | CH$_3$O(10) | H | | | |
| 273 | CH$_3$O(4) | H | CH$_3$CO- | $-(CH_2)_2-$ | n-C$_3$H$_7$ | CH$_3$O(10) | H | | | |
| 274 | CH$_3$O(4) | H | CH$_3$CO- | $-(CH_2)_3-$ | n-C$_3$H$_7$ | CH$_3$O(10) | H | | | |

TABLE VI-continued

| | Column I | | | Column II | | | Column III | | | |
|---|---|---|---|---|---|---|---|---|---|---|
| Ex. No. | $R^4$ (position) | $R^5$ (position) | Q | Z | $R^2$ | | $R^4$ (position) | $R^5$ (position) | Q | Z | $R^2$ |
| 275 | $CH_3O(5)$ | H | $CH_3CO-O-$ (i.e. $\underset{\underset{CH_3CO}{\|}}{O}$) | $-CH_2-$ | phenyl | $CH_3O(9)$ | H | | | |
| 276 | $CH_3O(5)$ | H | $\underset{\underset{CH_3CO}{\|}}{O}$ | $-CH_2-$ | $n-C_4H_9$ | $CH_3O(9)$ | H | | | |
| 277 | $CH_3O(6)$ | H | $\underset{\underset{CH_3CO}{\|}}{O}$ | $-CH_2-$ | $n-C_3H_7$ | $CH_3O(8)$ | H | | | |
| 278 | $CH_3O(6)$ | H | $\underset{\underset{CH_3CO}{\|}}{O}$ | $-(CH_2)_2-$ | phenyl | $CH_3O(8)$ | H | | | |
| 279 | $CH_3O(7)$ | H | $\underset{\underset{CH_3CO}{\|}}{O}$ | $-CH_2-$ | $n-C_4H_9$ | $CH_3O(7)$ | H | | | |
| 280 | $CH_3O(7)$ | H | $\underset{\underset{CH_3CO}{\|}}{O}$ | $-(CH_2)_2-$ | phenyl | $CH_3O(7)$ | H | | | |
| 281 | $CH_3O(7)$ | Cl(4) | $\underset{\underset{CH_3CO}{\|}}{O}$ | $-(CH_2)_2-$ | $n-C_3H_7$ | $CH_3O(7)$ | Cl(10) | | | |
| 282 | $CH_3O(4)$ | H | $CH_3O$ | $-CH_2-$ | phenyl | $CH_3O(10)$ | H | | | |
| 283 | $CH_3O(5)$ | H | $s-C_4H_9O$ | $-\underset{\underset{CH_3}{\|}}{CH}CH_2-$ | $n-C_3H_7$ | $CH_3O(9)$ | H | | | |
| 284 | $C_2H_5(5)$ | $C_2H_5(6)$ | phenyl-O— | $-CH_2-$ | $i-C_4H_9$ | $C_2H_5(9)$ | $C_2H_5(8)$ | | | |
| 285 | Cl(6) | H | phenyl-$CH_2O-$ | $-(CH_2)_3-$ | phenyl | Cl(8) | H | | | |
| 286 | $CF_3(7)$ | H | $CH_3OCH_2-$ | $-CH_2-$ | $CH_2OCH_3$ | $CF_3(7)$ | H | | | |

EXAMPLES 287 TO 304

Following the procedure of Example 9, but substituting the compounds indicated in Column I, Table VII below for 3-diazooxindole, and the compounds indicated in Column II below for dimethylacetylene dicarboxylate in Example 9A, the compounds indicated in Column III are obtained.

TABLE VII

| | Column I | | | Column II | | | Column III | | | |
|---|---|---|---|---|---|---|---|---|---|---|
| Ex. No. | $R^4$ (position) | $R^5$ (position) | Q | $Z_1$ | $R^2$ | $R^4$ (position) | $R^5$ (position) | Q | $Z_1$ | $R^2$ |
| 287 | H | H | $\underset{\underset{CH_3OC}{\|}}{O}$ | — | phenyl | H | as per column I | $HOCH_2$ | as per column II | phenyl |
| 288 | H | H | $\underset{\underset{C_2H_5OC}{\|}}{O}$ | — | $n-C_3H_7$ | H | | $HOCH_2$ | | $n-C_3H_7$ |
| 289 | H | H | $\underset{\underset{CH_3C}{\|}}{O}$ | — | phenyl-$OC_2H_5$ | H | | $\underset{\underset{CH_3}{\|}}{HOCH}-$ | | phenyl-$OC_2H_5$ |
| 290 | $CH_3O(4)$ | H | $\underset{\underset{HC}{\|}}{O}$ | — | phenyl | $CH_3O(10)$ | | $HOCH_2$ | | phenyl |
| 291 | $CH_3O(4)$ | H | $\underset{\underset{HC}{\|}}{O}$ | — | $s-C_4H_9$ | $CH_3O(10)$ | | $HOCH_2$ | | $n-C_3H_7$ |

TABLE VII-continued

| | Column I | | | Column II | | | Column III | | |
|---|---|---|---|---|---|---|---|---|---|
| Ex. No. | $R^4$ (position) | $R^5$ (position) | Q | $Z_1$ | $R^2$ | $R^4$ (position) | $R^5$ (position) | Q | $Z_1$ | $R^2$ |
| 292 | $CH_3O(5)$ | H | $CH_3OC(O)$ | — | phenyl-$CF_3$ | $CH_3O(9)$ | | $HOCH_2$ | | phenyl-$CF_3$ |
| 293 | $CH_3O(4)$ | H | $CH_3OC(O)$ | $-CH_2-$ | phenyl | $CH_3O(10)$ | | $HO(CH_2)_2$ | | phenyl |
| 294 | $CH_3O(6)$ | H | $CH_3C(O)$ | — | phenyl-$CH_3$ | $CH_3O(8)$ | | $HOCH(CH_3)$ | | phenyl-$CH_3$ |
| 295 | H | H | $CH_3OC(O)$ | $-CH_2-$ | phenyl | H | | $HO(CH_2)_2$ | | phenyl |
| 296 | H | H | $C_7H_{15}OC(O)$ | — | n-$C_3H_7$ | H | | $HOCH_2$ | | n-$C_3H_7$ |
| 297 | H | H | $CH_3C(O)$ | $-CH_2-$ | phenyl-$OC_2H_5$ | H | | $HOCHCH_2$ ($CH_3$) | | phenyl-$OC_2H_5$ |
| 298 | $CH_3O(4)$ | H | $HC(O)$ | $-(CH_2)_2-$ | phenyl | $CH_3O(10)$ | | $HO(CH_2)_3$ | | phenyl |
| 299 | $CH_3O(4)$ | H | $HC(O)$ | $-CH(CH_3)-$ | s-$C_4H_9$ | $CH_3O(10)$ | | $HOCH_2CH(CH_3)$ | | s-$C_4H_9$ |
| 300 | $CH_3O(5)$ | H | $CH_3OC(O)$ | — | phenyl-$CF_3$ | $CH_3O(9)$ | | $HOCH_2$ | | phenyl-$CF_3$ |
| 301 | $CH_3O(4)$ | H | $CH_3OC(O)$ | $-CH_2-$ | phenyl | $CH_3O(10)$ | | $HO(CH_2)_2$ | | phenyl |
| 302 | $CH_3O(6)$ | H | $CH_3C(O)$ | $-CH_2-$ | phenyl-$CH_3$ | $CH_3O(8)$ | | $HOCHCH_2(CH_3)$ | | phenyl-$CH_3$ |
| 303 | F(5) | H | $CH_3OC(O)$ | — | $C_4H_9$ | F(9) | H | $HOCH_2$ | — | $C_4H_9$ |
| 304 | $CH_3(5)$ | $CH_3(6)$ | $CH_3OC(O)$ | — | phenyl | $CH_3(9)$ | $CH_3(8)$ | $HOCH_2$ | — | phenyl |

EXAMPLES 305 TO 322

Following the procedure of Example 10, but substituting the compounds indicated in Column I, Table VIII below for 2-(hydroxymethyl)pyrazolo[1,5-c]-quinazolin-5(6H)-one in Example 10, the compounds indicated in Column II are obtained.

TABLE VIII

| | Column I | | | | | Column II | | | |
|---|---|---|---|---|---|---|---|---|---|
| Ex. No. | $R^4$ | $R^5$ | $R^1$ | $R^2$ | | $R^4$ | $R^5$ | $R^1$ | $R^2$ |
| 305 | H | H | H | $-CHOH(CH_3)$ | | as per column I | | H | $-CHOC(O)CH_3$ ($CH_3$) |

TABLE VIII-continued

| | Column I | | | | | Column II | | |
|---|---|---|---|---|---|---|---|---|
| Ex. No. | $R^4$ | $R^5$ | $R^1$ | $R^2$ | $R^4$ | $R^5$ | $R^1$ | $R^2$ |
| 306 | H | H | H | $-\underset{\underset{CH_3}{\mid}}{\overset{\overset{CH_3}{\mid}}{C}}OH$ | | H | | $-\underset{\underset{CH_3}{\mid}}{\overset{\overset{CH_3}{\mid}}{C}}\overset{O}{\overset{\parallel}{O}}CCH_3$ |
| 307 | H | H | H | $-CHOH$-Ph | | H | | $-CH(Ph)O\overset{O}{\overset{\parallel}{C}}CH_3$ |
| 308 | H | H | $HO(CH_2)_2$ | $-(CH_2)_2OH$ | $CH_3\overset{O}{\overset{\parallel}{C}}O(CH_2)_2$ | | | $-(CH_2)_2O\overset{O}{\overset{\parallel}{C}}CH_3$ |
| 309 | H | H | H | Ph-OH | | H | | Ph-$O\overset{O}{\overset{\parallel}{C}}CH_3$ |
| 310 | H | H | H | $-(CH_2)_2OH$ | as per column I except for Ex. 313 | H | | $-(CH_2)_2O\overset{O}{\overset{\parallel}{C}}CH_3$ |
| 311 | H | H | H | $-(CH_2)_3OH$ | | H | | $-(CH_2)_4O\overset{O}{\overset{\parallel}{C}}CH_3$ |
| 312 | H | H | H | $-(CH_2)_4OH$ | | H | | $-(CH_2)_3O\overset{O}{\overset{\parallel}{C}}CH_3$ |
| 313 | HO(9) | H | H | $-CH_2OH$ | $CH_3\overset{O}{\overset{\parallel}{C}}O(9)$ | H | | $-CH_2O\overset{O}{\overset{\parallel}{C}}CH_3$ |
| 314 | $CH_3O(9)$ | H | H | $-CH_2OH$ | | H | | $-CH_2O\overset{O}{\overset{\parallel}{C}}CH_3$ |
| 315 | $CH_3O(10)$ | H | $CH_3$ | $-\underset{\underset{CH_3}{\mid}}{\overset{\overset{CH_3}{\mid}}{C}}OH$ | | $CH_3$ | | $-\underset{\underset{CH_3}{\mid}}{\overset{\overset{CH_3}{\mid}}{C}}O\overset{O}{\overset{\parallel}{C}}CH_3$ |
| 316 | $CH_3O(10)$ | H | H | $-CH_2OH$ | | H | | $-CH_2O\overset{O}{\overset{\parallel}{C}}CH_3$ |
| 317 | $CH_3(10)$ | H | H | $-\underset{\underset{CH_3}{\mid}}{CH}CH_2OH$ | | H | | $-\underset{\underset{CH_3}{\mid}}{CH}CH_2O\overset{O}{\overset{\parallel}{C}}CH_3$ |
| 318 | $CH_3O(10)$ | H | H | $-(CH_2)OH$ | | H | | $-(CH_2)_2O\overset{O}{\overset{\parallel}{C}}CH_3$ |
| 319 | $C_2H_5O(9)$ | H | H | $-\underset{\underset{C_2H_5}{\mid}}{CH}CH_2OH$ | | H | | $-\underset{\underset{C_2H_5}{\mid}}{CH}CH_2O\overset{O}{\overset{\parallel}{C}}CH_3$ |

TABLE VIII-continued

| | Column I | | | | Column II | | |
|---|---|---|---|---|---|---|---|
| Ex. No. | $R^4$ | $R^5$ | $R^1$ | $R^2$ | $R^4$ $R^5$ $R^1$ | | $R^2$ |
| 320 | $CH_3O(9)$ | H | H | $-\underset{\underset{CH_3}{\mid}}{CHOH}$ | H | | $-\underset{\underset{CH_3}{\mid}}{CH}\overset{O}{\overset{\|}{-}}OCCH_3$ |
| 321 | $CH_3O(8)$ | H | $CH_3$ | $-CH_2OH$ | $CH_3$ | | $-CH_2O\overset{O}{\overset{\|}{C}}CH_3$ |
| 322 | $CH_3O(7)$ | H | H | $-(CH_2)_2OH$ | H | | $-(CH_2)_2O\overset{O}{\overset{\|}{C}}CH_3$ |

EXAMPLES 323 TO 343

Following the procedure of Example 10, but substituting the compounds indicated in Column I, Table IX below for 2-hydroxymethyl)pyrazolo[1,5-c]quinazolin-5(6H)-one and the acids indicated in Column II below for acetic acid in Example 10, the compounds indicated in Column III are obtained.

TABLE IX

| | Column I | | | | | Column II | Column III | | | |
|---|---|---|---|---|---|---|---|---|---|---|
| Ex. No. | $R^4$ (position) | $R^5$ (position) | $R^1$ | Z | | $R^9$ | $R^4$ (position) | $R^5$ (position) | $R^1$ Z | $R^9$ |
| 323 | OH(8) | OH(8) | $CH_3$ | $-CH_2-$ | | $CH_3$ | $\underset{CH_3CO-}{\overset{O}{\overset{\|}{}}}$ | $\underset{CH_3CO-}{\overset{O}{\overset{\|}{}}}$ | | as in Column II |
| 324 | OH(7) | H | H | $-(CH_2)_2-$ | | H | $\underset{CH_3CO}{\overset{O}{\overset{\|}{}}}$ | H | | |
| 325 | $\underset{HCO(10)}{\overset{O}{\overset{\|}{}}}$ | H | H | $-(CH_2)_3-$ | | $C_2H_5$ | | | | as in Column I |
| 326 | $CH_3(10)$ | $CH_3O(9)$ | H | $-CH_2-$ | | H | | | | |
| 327 | $C_2H_5(8)$ | $C_2H_5(9)$ | H | $-\underset{\underset{CH_3}{\mid}}{CH}-$ | | $-CH_2\text{-}C_6H_5$ | | | | |
| 328 | $CH_3O(10)$ | H | H | $-CH_2-$ | | $-CH_3$ | | | | |
| 329 | $CH_3O(10)$ | H | H | $-\underset{\underset{CH_3}{\mid}}{\overset{CH_3}{\overset{\mid}{C}}}-$ | | $n\text{-}C_3H_7$ | | | | |
| 330 | $CH_3O(9)$ | H | $CH_3$ | $-CH_2-\underset{\underset{}{}}{\overset{CH_3}{\overset{\mid}{CH}}}-$ | | $-C_6H_5$ | | | | |
| 331 | $CH_3O(9)$ | H | H | $-CH_2-\underset{\underset{CH_3}{\mid}}{\overset{CH_3}{\overset{\mid}{C}}}-CH_2-$ | | $-CH_2\text{-}C_6H_4\text{-}CH_3$ | | | | |
| 332 | $CH_3O(9)$ | H | $CH_3$ | $-CH_2-$ | | $-CH_2\text{-}C_6H_4\text{-}Cl$ | | | | |
| 333 | $CH_3O(7)$ | H | H | $-CH_2-$ | | $n\text{-}C_4H_9$ | | | | |
| 334 | $CH_3O(7)$ | Cl(4) | H | cyclohexyl-C(CH_3) | | $CH_3$ | | | | |
| 335 | F(9) | H | H | $-\underset{\underset{C_2H_5}{\mid}}{CH}-$ | | $C_2H_5$ | | | | |

TABLE IX-continued

| | Column I | | | | Column II | | Column III | | | | |
|---|---|---|---|---|---|---|---|---|---|---|---|
| Ex. No. | R⁴ (position) | R⁵ (position) | $R^1$ | Z | $R^9$ | | R⁴ (position) | R⁵ (position) | $R^1$ | Z | $R^9$ |
| 336 | Br(9) | H | $C_2H_5$ | $-CH_2-\overset{CH_3}{\underset{\|}{CH}}-$ | i-$C_4H_9$ | | | | | | |
| 337 | Br(9) | Br(8) | H | (cyclobutyl-CH) | H | | | | | | |
| 338 | $CF_3$(7) | H | $CH_3$ | (cyclohexyl-CH) | $CH_3$ | | | | | | |
| 339 | $NO_2$(9) | H | H | $-CH_2-$ | i-$C_2H_5$ | | | | | | |
| 340 | H | H | $CH_3$ | $-(CH_2)_3-$ | s-$C_4H_9$ | | | | | | |
| 341 | H | H | $CH_3$ | $-\overset{CH_3}{\underset{\|}{CH}}-CH_2-$ | $CH_3$ | | | | | | |
| 342 | H | H | H | $-\overset{Ph}{\underset{\|}{CH}}-$ | $CH_3$ | | | | | | |

EXAMPLES 343 to 383

Following the procedure of Example 22 or 23, but substituting the compounds indicated in Column I, Table X, below for 3-diazooxindole and the compounds indicated in Column II below for propargyl alcohol in Example 22 or 23, the compounds indicated in Column III are obtained.

TABLE X

| | Column I | | | Column II | | Column III | | |
|---|---|---|---|---|---|---|---|---|
| | (diazo-indolinone structure) | | | $R^1-C\equiv C-Z-OR^6$ | | (vinyl-indolinone structure) | | |
| Ex. No. | $R^4$ (position) | $R^5$ (position) | $R^1$ | $Z-OR^6$ | | $R^4$ (position) | $R^5$ (position) | $R^1$ $Z-OR^6$ |
| 343 | OH(6) | OH(5) | CH$_3$ | CH$_2$OH | | OH(8) | OH(9) | as in Column II |
| 344 | OH(5) | H | H | (CH$_2$)$_2$OH | | OH(9) | H | |
| 345 | | H | H | (CH$_2$)$_3$OH | | | H | |
| 346 | CH$_3$CO(4) | CH$_3$O(5) | H | CH$_2$OH | | CH$_3$CO(10) | CH$_3$O(9) | H |
| 347 | CH$_3$(4) C$_2$H$_5$(5) | C$_2$H$_5$(6) | H | —CHOH CH$_3$ | | CH$_3$(10) C$_2$H$_5$(9) | CH$_3$O(9) C$_2$H$_5$(8) | H |
| 348 | CH$_3$O(4) | H | H | —CHOH CH$_3$ | | CH$_3$O(10) | H | H |
| 349 | CH$_3$O(4) | H | H | —COH CH$_3$ CH$_3$ | | CH$_3$O(10) | H | H |
| 350 | CH$_3$O(5) | H | CH$_3$ | —CH$_2$—CHOH CH$_3$ | | CH$_3$O(9) | H | H |
| 351 | CH$_3$O(6) | H | H | —CH$_2$—C—CH$_2$OH CH$_3$ | | CH$_3$O(8) | H | H |
| 352 | CH$_3$O(5) | H | CH$_3$ | CH$_3$OH | | CH$_3$O(9) | H | H |
| 353 | CH$_3$O(5) | H | H | CH$_2$OH | | CH$_3$O(9) | H | H |
| 354 | CH$_3$O(7) | Cl(4) | H | (cyclohexyl with OH, C$_2$H$_5$) | | CH$_3$O(7) | Cl(10) | H |
| 355 | F(6) | H | H | —CH—OH CH$_3$ | | F(8) | H | H |
| 356 | Br(5) | H | C$_2$H$_5$ | —CH$_2$—CHOH CH$_3$ | | Br(9) | H | H |
| 357 | Br(5) | Br(6) | H | (cyclohexyl with OH) | | Br(9) | Br(6) | Br(8) |
| 358 | CF$_3$(7) | H | CH$_3$ | (cyclohexyl with OH, CH$_2$OH) | | CF$_3$(7) | H | H |
| 359 | NO$_2$(5) | H | C$_2$H$_5$ | CH$_2$OH | | NO$_2$(9) | H | H |

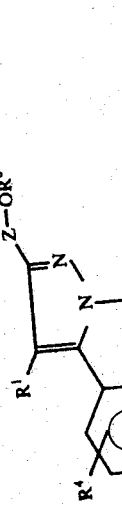

TABLE X-continued

| Ex. No. | Column I (R⁴ position) | R⁵ (position) | Column II R¹ | Z—OR⁶ | Column III R⁴ (position) | R⁵ (position) | R¹ |
|---|---|---|---|---|---|---|---|
| 360 | H | H | CH₃ | —(CH₂)₃OH | H | H | H |
| 361 | H | H | CH₃ | —CH—CH₂OH, CH₃ | H | H | H |
| 362 | CH₃(5) | H | CH₃ | —CH₂—OCCH₃, O | CH₃(9) | H | H |
| 363 | i-C₃H₇(5) | H | H | —CH₂—OCCH₃, O | i-C₃H₇(9) | H | H |
| 364 | CH₃(5) | CH₃(6) | H | —(CH₂)₂OCCH₃, O | CH₃(9) | CH₃(8) | H |
| 365 | CH₃O(4) | H | CH₃ | —CH₂—OC—C₆H₅, O | CH₃O(10) | H | H |
| 366 | CH₃O(4) | H | H | CH₂OCCH₃, CH₂—OC₂H₅, O | CH₃O(10) | H | H |
| 367 | CH₃O(4) | H | H | CH₂OCCH₃, CH₂—OCCH₃, O | CH₃O(10) | H | H |
| 368 | C₂H₅O(5) | H | H | CH₂—OC₆H₅, O | C₂H₅O(9) | H | H |
| 369 | CH₃O(5) | H | H | (CH₂)₂OCC₂H₅, O | CH₃O(9) | H | H |
| 370 | CH₃O(6) | H | H | CH₂OC—C₆H₄—CH₃, O | CH₃O(8) | H | H |
| 371 | Cl(5) | H | H | —CH₂OCCH₂—O—OCH₃, O | Cl(9) | H | H |
| 372 | OH(4) | OH(5) | H | —(CH₂)₃OCH₃ | OH(10) | OH(9) | H |
|  |  | H |  | —CH₂OCH₂—C₆H₅ | H | H |  |

TABLE X-continued

| | Column I | | | Column II | | Column III | | |
|---|---|---|---|---|---|---|---|---|
| Ex. No. | R⁴ (position) | R⁵ (position) | R¹ | R¹—C≡C—Z—OR⁶ Z—OR⁶ | | R⁴ (position) | R⁵ (position) | R¹ Z—OR⁶ |
| 374 | H | H | H | | | H | H | H |
| 375 | H | H | H | | | H | H | H |
| 376 | H | H | CH₃ | —CH(CH₃)OCOC₂H₅ | | H | H | H |
| 377 | H | H | CH₃OCH₂ | | | H | H | H |
| 378 | H | H | C₂H₅ | | | H | H | H |
| 379 | CH₃CO(7) | H | H | —CHOCCH₃ (with C₆H₅) | | CH₃CO(7) | H | H |
| 380 | CH₃ / CH₂O(6) Br(5) | H | CH₃CO(CH₂)₂ | —OCH₃, —CH₂OCH₃, —CH₂—C(CH₃)(OCC₂H₅)—CH₂O nC₄H₉ | | CH₃ / Br(9) | H | H |
| 381 | F(6) | H | H | —(CH₂)₂OCCH₃ / CH₃, —C(OCH₃)(C₂H₅)— | | F(8) | CH₃O(8) | H |
| 382 | Cl(6) | H | CH₃ | —(CH₂)₂OCH | | Cl(8) | H | H |
| 383 | CF₃(5) | H | CH₃COCH₂ | CH₂OCCH₃ | | CF₃(9) | H | H |

EXAMPLES 384 to 424

Following the procedure of Example 2A, but substituting for 3-diazooxindole the compound shown in column I of Table XI below and substituting for ethyl propiolate the compound shown in column II below, and thereafter treating the resulting ester in the manner set out in Example 2B the compound of the invention shown in Column III is obtained.

TABLE XI

| | Column I | | | Column II | | | Column III | | |
|---|---|---|---|---|---|---|---|---|---|
| | (diazo-oxoindoline structure with $R^4$, $R^5$) | | | $R^1-C≡C-Z_1-COR^9$ | | | (structure with $R^1$, $R^4$, $R^5$, Z-CH$_2$OH) | | |
| Ex. No. | $R^4$ (position) | $R^5$ (position) | $R^1$ | $Z_1$ | $R^9$ | $R^4$ (position) | $R^5$ (position) | $R^1$ | $Z_1$ |
| 384 | t-C$_4$H$_9$(5) | H | H | —(CH$_2$)$_2$— | C$_5$H$_{11}$ | t-C$_4$H$_9$(9) | H | as in column II | |
| 385 | CH$_3$(7) | CH$_3$(6) | CH$_3$ | —CH$_2$— | C$_{10}$H$_{21}$ | CH$_3$(7) | CH$_3$(8) | HO(CH$_2$)$_2$ | |
| 386 | i-C$_3$H$_7$(5) | H | C$_4$H$_9$OC(=O)—CH$_2$ | —CH$_2$— | C$_4$H$_9$ | i-C$_3$H$_7$(9) | H | as in column II | |
| 387 | CH$_3$(5) | CH$_3$(6) | H | —CH(CH$_3$)—CH$_2$CH$_2$— | CH$_3$ | CH$_3$(9) | CH$_3$(8) | " | |
| 388 | C$_2$H$_5$(4) | H | H | —CH$_2$— | CH$_2$—C$_6$H$_5$ | C$_2$H$_5$(10) | H | " | |
| 389 | CH$_3$O(4) | H | H | —CH$_2$—C(CH$_3$)$_2$—CH$_2$— | CH$_3$ | CH$_3$O(10) | H | HOCH$_2$ | |
| 390 | C$_2$H$_5$O(5) | H | CH$_3$OC(=O) | —CH$_2$— | CH$_3$ | C$_2$H$_5$O(9) | H | HOCH$_2$ | |
| 391 | CH$_3$O(4) | H | CH$_3$ | —CH$_2$— | C$_5$H$_{11}$ | CH$_3$O(10) | H | as in column II | |
| 392 | OH(5) | OH(6) | H | —CH(CH$_2$)$_3$— | CH$_3$ | OH(9) | OH(8) | " | |
| 393 | OH(5) | OCH$_3$(7) | H | —(CH$_2$)$_2$— | C$_2$H$_5$ | OH(9) | OCH$_3$(7) | " | |
| 394 | OH(5) | H | C$_2$H$_5$ | —(CH$_2$)$_3$— | CH$_2$—C$_6$H$_4$—CH$_3$ (p) | OH(9) | H | HOCH$_2$ | |
| 395 | CH$_3$O(5) | H | H | —CH$_2$— | CH$_3$ | CH$_3$O(9) | H | HOCH$_2$ | |
| 396 | C$_6$H$_5$—CH$_2$—O(5) | H | CH$_3$OC(=O) | —C(CH$_3$)$_2$— | C$_2$H$_5$ | C$_6$H$_5$—CH$_2$—O(9) | H | HOCH$_2$ | |
| 397 | Br(5) | H | C$_2$H$_5$OC(=O) | —CH$_2$— | C$_2$H$_5$ | Br(9) | H | as in column II | |
| 398 | Cl(4) | CH$_3$(7) | H | —CH$_2$— | C$_6$H$_{13}$ | Cl(10) | CH$_3$(7) | as in column II | |
| 399 | Cl(6) | H | CH$_3$OC(=O) | —(CH$_2$)$_2$— | C$_4$H$_9$—CH$_2$—C$_6$H$_4$—OCH$_3$ (p) | Cl(8) | H | HOCH$_2$ | |
| 400 | CF$_3$(7) | H | CH$_3$ | —CH$_2$—CH(C$_2$H$_5$)— | CH$_3$ | CF$_3$(7) | H | as in column II | |
| 401 | CF$_3$(5) | CF$_3$(6) | CH$_3$ | —CH$_2$— | C$_6$H$_5$ | CF$_3$(9) | CF$_3$(8) | as in column II | |

TABLE XI-continued

| | Column I | | | | Column II $R^1-C\equiv C-Z_1COR^9$ | | | Column III | | |
|---|---|---|---|---|---|---|---|---|---|---|
| Ex. No. | $R^4$ (position) | $R^5$ (position) | $R^1$ | $Z_1$ | $R^9$ | $R^4$ (position) | $R^5$ (position) | $R^1$ | $Z_1$ | |
| 402 | F(5) | H | H | —CH$_2$— | p-tolyl | F(9) | H | HOCH$_2$ | | |
| 403 | H | H | $\begin{matrix}O\\\|\|\\\text{—O—C—CH}_3\end{matrix}$ (phenyl) | | CH$_3$ | H | H | as in column II | | |
| 404 | H | H | H | $\begin{matrix}C_2H_5\\\|\\-CH_2-CH-CH_2\end{matrix}$ | CH$_3$ | H | H | | | |
| 405 | t-C$_4$H$_9$(5) | H | H | —(CH$_2$)$_3$— | C$_5$H$_{11}$ | t-C$_4$H$_9$(9) | H | | | |
| 406 | CH$_3$(7) | CH$_3$(6) | CH$_3$ | = | C$_{10}$H$_{21}$ | CH$_3$(7) | CH$_{3(8)}$ | | | |
| 407 | i-C$_3$H$_7$(6) | H | H | = | C$_4$H$_9$ | i-C$_3$H$_7$(8) | H | | | |
| 408 | CH$_3$(5) | CH$_3$(6) | C$_2$H$_5$OC—CH$_2$ | = | CH$_3$ | CH$_3$(9) | H | as in column II | | |
| 409 | C$_2$H$_5$(4) | H | H | = | CH$_2$(phenyl) | C$_4$H$_9$(10) | H | | | |
| 410 | CH$_3$O(4) | OH(6) | H | = | CH$_3$ | CH$_3$O(10) | H | | | |
| 411 | C$_2$H$_5$O(5) | OCH$_3$(7) | $\begin{matrix}O\\\|\|\\CH_3OC—\end{matrix}$ | = | CH$_3$ | C$_2$H$_5$O(9) | H | | | |
| 412 | CH$_3$O(4) | OH(6) | CH$_3$ | = | CH$_3$ (p-tolyl) | CH$_3$O(10) | H | | | |
| 413 | OH(6) | OCH$_3$(7) | H | = | C$_2$H$_5$ | CH$_2$OH(9) | H | | | |
| 414 | OH(5) | H | C$_2$H$_5$ | = | CH$_2$(phenyl) | OH(8) | OH(8) | | | |
| 415 | | | | | CH$_3$ | OH(9) | OCH$_3$(7) | | | |
| 416 | CH$_3$O(5) | H | $\begin{matrix}O\\\|\|\\CH_3OC—\end{matrix}$ | — | C$_2$H$_5$ | CH$_3$O(9) | H | | | |
| 417 | CH$_2$—O(5) (benzyl) | H | CH$_3$ | — | C$_6$H$_{13}$ (p-methoxyphenyl) | CH$_2$—O(9) (benzyl) | H | | | |
| 418 | Br(5) | H | $\begin{matrix}O\\\|\|\\C_2H_5OC—\end{matrix}$ | — | CH$_2$(phenyl) | Br(9) | H | | | |
| 419 | Cl(4) | CH$_3$(7) | H | — | C$_4$H$_9$ | Cl(10) | H | | | |
| 420 | Cl(5) | H | H | — | CH$_3$ | Cl(9) | H | CH$_3$(7) | | |
| 421 | CF$_3$(7) | H | H | — | (phenyl) | CF$_3$(7) | H | | | |
| 422 | CF$_3$(5) | CF$_3$(6) | CH$_3$ | — | (p-tolyl) | CF$_3$(9) | CF$_3$(8) | as per column II | | |
| 423 | F(5) | H | CH$_3$ | — | CH$_3$ | F(9) | H | | | |
| 424 | H | H | H | — | CH$_3$ | H | H | | | |

EXAMPLES 425 to 445

Following the procedure of Example 10, but substituting the compounds indicated in Column I, Table XII below for 2-(hydroxymethyl)pyrazolo[1,5-c]quinazolin-5(6H)-one and the acids indicated in Column II below for acetic acid in Example 10, the compounds indicated in Column III are obtained.

EXAMPLE 426

9-Fluoro-2-(hydroxymethyl)pyrazolo[1,5-c]quinazolin-5(6H)-one

A. p-Toluenesulfonyl hydrazone of 5-Fluoroisatin 10 g (0.061 mole) of 5-fluoroisatin (red powder) is dissolved in methanol (280 ml) at 60° and treated portionwise with 12.3 g of 97% toluenesulfonyl hydrazine (1.05 equiv or 0.064 mole). The mixture is stirred at 60° for 15–20 minutes and then at room temperature for 20 hours under nitrogen. The reaction mixture is concen-

| | Column I | | | | Column II | Column III | | | | |
|---|---|---|---|---|---|---|---|---|---|---|
| | 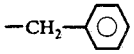 | | | |  |  | | | | |
| Ex. No. | R⁴ (position) | R⁵ (position) | R¹ | Z | R⁹ | R⁴ (position) | R⁵ (position) | R¹ | Z | R⁹ |
| 425 | H | H | CH₃ | —CH₂— | CH₃ | as in column I | | | | as in Column II |
| 426 | H | H | H | —(CH₂)₂— | H | | | | | |
| 427 | H | H | H | —(CH₂)₃— | C₂H₅ | | | | | |
| 428 | CH₃(10) | H | H | —CH₂— | n-C₃H₇ | | | | | |
| 429 | H | H | H | CH₃<br>\|<br>—CH— | —CH₂— | | | | | |
| 430 | CH₃O(10) | H | H | —CH₂— | C₂H₅ | | | | | |
| 431 | CH₃O(10) | H | H | CH₃<br>\|<br>—CH—<br>\|<br>CH₃—CH₂— | s-C₄H₉ | | | | | |
| 432 | CH₃O(10) | H | H | —CH₂— | —CH₂— | | | | | |
| 433 | C₂H₅O(9) | H | CH₃ | CH₃<br>\|<br>—CH₂—CH— |  | | | | | |
| 434 | H | H | H | CH₃<br>\|<br>—CH₂—C—CH₂—<br>\|<br>CH₃ | —CH₃ | | | | | |
| 435 | CH₃O (5) | H | CH₃ | —CH₂— | —CH₂——Cl | | | | | |
| 436 | CH₃O(7) | H | H | —CH₂— | n-C₄H₉ | | | | | |
| 437 | H | H | H |  | CH₃ | | | | | |
| 438 | F(9) | H | H | C₂H₅<br>\|<br>—CH— | C₂H₅ | | | | | |
| 439 | CH₃(9) | H | C₂H₅ | CH₃<br>\|<br>—CH₂—CH— | i-C₄H₉ | | | | | |
| 440 | CH₃(8) | CH₃(9) | H | | H | | | | | |
| 441 | CF₃(7) | H | CH₃ | | CH₃ | | | | | |
| 442 | NH₂ | H | H | —CH₂— | i-C₃H₇ | | | | | |
| 443 | H | H | CH₃ | —(CH₂)₃— | s-C₄H₉ | | | | | |
| 444 | H | H | CH₃ | CH₃<br>\|<br>—CH—CH₂— | CH₃ | | | | | |
| 445 | H | H | H | —CH—<br>\|<br>⌬ | CH₃ | | | | | | trated to ½ its original volumne and the bright yellow precipitates are filtered off and dried in vacuo for 1-½ hours at 45°. Yield: 16.3 g, m.p. 205°–207°; 80% crude yield. The crude product is then taken up in dioxane (500 ml) and the resulting solution concentrated down to a volume of 150 ml. The solution is cooled and the yellow precipitates are filtered off and washed with small amount of methanol. The product is dried in vacuo at 55° for 20 hours to yield: 13.6 g, m.p. 210°–211° of the title compound.

B. 5-Fluoro-3-diazooxindole 12.0 g (0.036 mole) of the tosyl hydrazone from Part A is dissolved in 410 ml of 0.2 N NaOH with slight heating over a period of 1 hour and then stirred at room temperature for 2 hours. The reaction mixture is then saturated with $CO_2$ (dry ice used), stirred for 30 minutes and the light orange precipitates are filtered off and dried in vacuo at 45° for 3 hours. Yield: 6.2 g, m.p. 209°–210°; 97.2% crude yield. The crude product is taken up in methanol (300 ml) and the clear red solution concentrated down to a volume of 100 ml.

The red precipitates are filtered off and dried overnight in vacuo at 55° to yield the title B compound.

C. 9-Fluoro-2-(hydroxymethyl)pyrazolo[1,5-c]quinazolin-5(6H)-one 2.0 g (0.0113 mole) of 5- fluoro-3-diazooxindole (part B) and 13.1 g (0.226 mole of 20 equivalents) of 97% propargyl alcohol are refluxed under argon for 4 hours. The reaction mixture is cooled, diluted with ether (200 ml) and stirred for 15 minutes. The beige-colored precipitates are filtered off and dried in vacuo overnight. Yield: 2.3 g, mp 295°–297°, 87.5% crude yield. The crude produce is taken up in absolute ethanol (500 ml), treated with activated carbon, filtered through a Celite pad, the pad is washed with 50 ml of hot ethanol. The clear filtrate is concentrated down to a volume of 100 ml and cooled. The white precipitates are filtered off and dried in vacuo at 60° to yield the product (title compound) 1.16 g, mp 303°–304°.

What is claimed is:

1. A compound of the structure

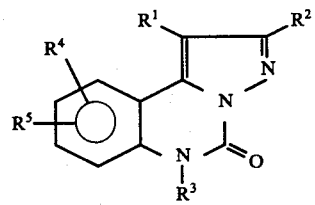

wherein $R^1$ and $R^2$ are the same or different, and $R^1$ is selected from the group consisting of hydrogen, lower alkyl, phenyl, phenyl having an $R^4$ substituent, or

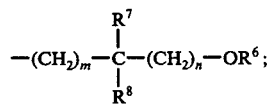

$R^2$ is selected from the group consisting of

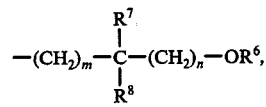

hydrogen, lower alkyl, phenyl or phenyl having an $R^2$ substitutent, with the proviso that at least one of $R^1$ and $R^2$ is

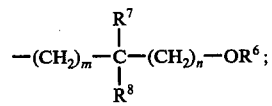

$R^6$ is selected from the group consisting of

having 1 to 8 carbons in the alkyl group,

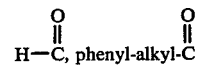

having 1 to 8 carbons in the alkyl group or

wherein phenyl includes unsubstituted phenyl, mono-, or di-lower-alkylphenyl, or halophenyl;

$R^3$ is selected from the group consisting of hydrogen, lower alkyl, benzyl, phenyl, or phenyl having an $R^4$ sustituent;

$R^4$ and $R^5$ are the same or different and are selected from the group consisting of hydrogen, alkyl of 1 to 4 carbons, alkoxy of 1 to 4 carbons, lower alkanoyloxy of 1 to 4 carbons, nitro, benzyloxy, benzyloxy having a lower alkoxy, halogen, hydroxy, or trifluoromethyl substituent;

$R^7$ and $R^8$ may be the same or different and are selected from the group consisting of hydrogen, alkyl of 1 to 3 carbons, phenyl, phenyl having a lower alkoxy substituent, benzyl, or benzyl having a lower alkoxy substituent, or $R^7$ and $R^8$ taken together is a single cycloalkyl ring of 3 to 7 carbons;

$(CH_2)_m$ and $(CH_2)_n$ represent straight chain alkylene radicals or mono- or di-alkyl substituted alkylene radicals wherein the alkyl group has 1 to 8 carbons, $m$ and $n$ are integers which represent the number of carbon atoms in the longest normal chains and may be the same or different and are 0 to 10, with the proviso that $m + n \leq 10$, and physiologically acceptable salts thereof.

2. The compound of claim 1 wherein $R^1$ is hydrogen or

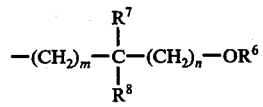

wherein $R^6$ is and R² is

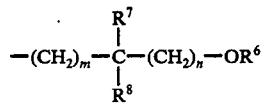

wherein R⁶ is

3. The compound of claim 2 wherein R³ is hydrogen or lower alkyl, R⁴ and R⁵ are hydrogen, or one of R⁴ and R⁵ is halogen or lower alkoxy.

4. The compound of claim 2 wherein R¹ is hydrogen and R² is selected from the group consisting of

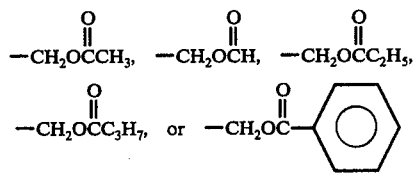

5. The compound of claim 4 wherein R³ is hydrogen, and R⁵ is 7-, 8-, 9- or 10-Cl, 7-, 8-, 9- or 10—OCH₃, or 8- or 9—CH₃, 9-F, or 7-CF₃.

6. The compound as defined in claim 5 wherein R⁵ is 7-OCH₃ and R⁴ is 10-Cl.

7. The compound as defined in claim 4 having the structure

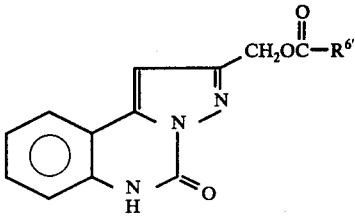

wherein R⁶' is alkyl of 1 to 4 carbons or hydrogen.

8. The compound as defined in claim 7 wherein alkyl is methyl.

9. The compound as defined in claim 7 wherein alkyl is ethyl or propyl.

10. A pharmaceutical composition for use in treating allergic conditions comprising a compound as defined in claim 1 and a pharmaceutically acceptable carrier therefor.

11. A method for treating allergic conditions in mammals, which comprises administering to the mammalian host a therapeutic amount of a compound as defined in claim 1.

* * * * *

Page 1 of 4
UNITED STATES PATENT OFFICE
CERTIFICATE OF CORRECTION

Patent No. 4,076,818    Dated February 28, 1978

Inventor(s) B. Richard Vogt

It is certified that error appears in the above-identified patent and that said Letters Patent are hereby corrected as shown below:

Column I, lines 7-15, before the structure insert --I--.
Column I, line 30, before the structure insert --$R^2$ is--.
Column 3, line 21, "1dower" should read --lower--.
Column 5, line 4, before the structure insert --$R_1^1$ is--.
Column 5, line 10, before the structure insert --$R_1^2$ is--.
Column 6, line 35, "resence" should read --presence--.
Column 6, line 39, "increase" should read --increases--.
Column 6, line 41, "abovede-" should read --above-de- --.
Column 6, line 57, "3ol" should read --3-ol--.
Column 8, line 19, "abovedescribed" should read --above-described--.
Column 9, line 24, after "Where $R_1^1$ or" insert --$R_1^2$ is--.
Column 19, line 36, "of" should read --or--.
Column 20, line 39, "2.1." should read --2 1.--.
Column 20, line 54, "[1.5-c]" should read --[1,5-c]--.
Column 22, line 66, "80.0057" should read --(0.0057--.
Column 23, line 48, "2[1-" should read --2-(1- --.
Column 23, line 50, "2acetyl-" should read --2-acetyl- --.
Column 24, line 46, "$Ch_3OH$" should read --$CH_3OH$--.
Column 24, line 47, "$CHCL_3$" should read --$CHCl_3$--.
Column 25, line 57, "$Bh_3$" should read --$BH_3$--.
Column 26, line 11, "utilized" should read --utilizing--.
Column 26, line 56, "83.0" should read --(3.0--.
Column 28, line 27, "18 30" should read --∿30--.
Column 32, line 53, "palladiumon" should read --palladium on--.
Column 33, line 8, "ether" should read --ethyl--.
Column 34, line 63, "48 ml" should read --480 ml--.

UNITED STATES PATENT OFFICE
CERTIFICATE OF CORRECTION

Patent No. 4,076,818  Dated February 28, 1978

Inventor(s) B. Richard Vogt

It is certified that error appears in the above-identified patent and that said Letters Patent are hereby corrected as shown below:

Columns 41-42, Table I, Column III, under headings "$R^1$ $Z_1$ $R^9$" insert --as per Column II--.

Columns 47-50, Table II, Column III, under heading "$R^3$" insert --as per Column I-- and under headings "$R^1$ $R^2$" insert --as per Column II--.

Columns 47-48, Table II, Example 100, Column II, under heading "$R^2$" the structure should read -- -CHOH $CH_2$-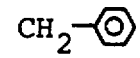 --.

Columns 55-62, Table III, Column IV, under heading "$R^3$" insert --as in Column I--.

Columns 61-62, Table III, Example 149, Column II, under heading "$R_1^2$" the structure should read -- -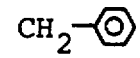 --.

Columns 67-68, Table V, Example 198, Column II, under heading $R^5$" insert --H--.

Columns 69-74, Table VI, Column III, under headings "Q Z $R^2$" insert --as per Column II--.

Columns 75-76, Table VII, Column III, under heading "$R^5$(position)" insert --as per Column I-- and under heading "$Z_1$" insert --as per Column II--.

Columns 77-80, Table VIII, Column II, under headings "$R^4$ $R^5$" insert --as per Column I--.

UNITED STATES PATENT OFFICE
CERTIFICATE OF CORRECTION

Patent No. 4,076,818  Dated February 28, 1978

Inventor(s) B. Richard Vogt

It is certified that error appears in the above-identified patent and that said Letters Patent are hereby corrected as shown below:

Columns 77-78, Table VIII, Example 309, Column I, under heading "$R^2$" the structure should read --  -- and Column II under heading "$R^2$" the structure should read -- -- .

Column 80, line 24, "2-hydroxymethyl)" should read --2-(hydroxymethyl)--.

Columns 79-80, Table IX, Example 331, Column II, the structure should read --  -- .

Columns 79-80, Table IX, Example 332, Column II, the structure should read --  -- .

Columns 81-82, Table IX, Column III, under headings "$R^4$(position) $R^5$(position) $R^1$ Z" insert --as in Column I-- and under heading "$R^9$" insert --as in Column II--.

Columns 85-88, Table X, Column III, under headings "$R^1$ Z-OR$^6$" insert --as per Column II--.

Column 96, line 1, "Example 426" should read --Example 446--.

Columns 95-96, before the table insert --TABLE XII--.

Columns 95-96, Table XII, Example 434, Column II, the structure should read -- -- .

UNITED STATES PATENT OFFICE
CERTIFICATE OF CORRECTION

Patent No. 4,076,818                    Dated February 28, 1978

Inventor(s) B. Richard Vogt

It is certified that error appears in the above-identified patent and that said Letters Patent are hereby corrected as shown below:

Column 97, line 32, "B9" should read --B)--.
Column 98, line 8, "$R^2$" should read --$R^4$--.
Column 98, line 53, "8" should read --2--.

Signed and Sealed this

Fourth Day of July 1978

[SEAL]

Attest:

RUTH C. MASON
*Attesting Officer*

DONALD W. BANNER
*Commissioner of Patents and Trademarks*